(12) United States Patent
Feys et al.

(10) Patent No.: US 12,310,989 B2
(45) Date of Patent: May 27, 2025

(54) METHODS FOR PREPARING PLATELET RELEASATE

(71) Applicant: ONDERZOEKS- EN ONTWIKKELINGSFONDS RODE KRUIS-VLAANDEREN, Mechelen (BE)

(72) Inventors: Hendrik B. Feys, Zwevegem (BE); Philippe Vandekerckhove, Holsbeek (BE); Veerle Compernolle, Veldegem (BE)

(73) Assignee: ONDERZOEKS- EN ONTWIKKELINGSFONDS RODE KRUIS-VLAANDEREN, Mechelen (BE)

( * ) Notice: Subject to any disclaimer, the term of this patent is extended or adjusted under 35 U.S.C. 154(b) by 898 days.

(21) Appl. No.: 17/293,825

(22) PCT Filed: Nov. 14, 2019

(86) PCT No.: PCT/EP2019/081257
§ 371 (c)(1),
(2) Date: May 13, 2021

(87) PCT Pub. No.: WO2020/099530
PCT Pub. Date: May 22, 2020

(65) Prior Publication Data
US 2022/0008475 A1    Jan. 13, 2022

(30) Foreign Application Priority Data
Nov. 14, 2018  (EP) .................................... 18206107

(51) Int. Cl.
*A61K 35/19*    (2015.01)
(52) U.S. Cl.
CPC ..................... *A61K 35/19* (2013.01)
(58) Field of Classification Search
CPC ..................................................... A61K 35/19
See application file for complete search history.

(56) References Cited

U.S. PATENT DOCUMENTS

| | | | |
|---|---|---|---|
| 9,011,687 B2 * | 4/2015 | Swift | B01D 17/0217 210/287 |
| 9,011,846 B2 | 4/2015 | Overholser et al. | |
| 2007/0184029 A1 | 8/2007 | Mishra | |
| 2012/0230967 A1 | 9/2012 | Long et al. | |

FOREIGN PATENT DOCUMENTS

| | | |
|---|---|---|
| JP | 2004-269409 A | 9/2004 |
| JP | 2013-522186 A | 6/2013 |
| JP | 2014-118362 A | 6/2014 |
| WO | WO 2004/103440 | 12/2004 |
| WO | WO 2011110948 | 9/2011 |
| WO | WO-2013003356 A1 * | 1/2013 .......... A61K 31/727 |
| WO | WO 2014/117140 A1 | 7/2014 |
| WO | WO2016/001624 | 1/2016 |

OTHER PUBLICATIONS

Michael F. Ashby, (Materials and the Environment (Second Edition), Elsevier Inc., Chapter 15, 2013), retrieved from internet Mar. 5, 2024. (Year: 2013).*
Kawatsu and Sato (Effect of Glass Contact on the Clotting Time of Carp Blood, Nippon Suisan Gakkaishi, 53(9), 1533-1536 (1987)) (Year: 1987).*
Husebekk, A. et al., Hepatitis B virus-infected peripheral blood progenitor cell harvests in liquid nitrogen freezer containing non-infectious products, Letters to The Editor, Transfusion vol. 44, pp. 942-951, 2004.
Su, C. Y., et al., Quantitative assessment of the kinetics of growth factors release from platelet gel, Transplantation and Cellular Engineering, Transfusion, vol. 48, pp. 2414-2420, 2008.
Bernardi, M. et al., The production method affects the efficacy of platelet derivatives to expand mesenchymal stromal cells in vitro, Journal of Translation Medicine, vol. 15, No. 19, 2017.
Chou, M. et al., Ex vivo Expansion of Bovine Corneal Endothelial Cells in Xeno-Free Medium Supplemented with Platelet Releasate, Public Library of Science, vol. 9, Issue 6, 2014.
International Preliminary Report On Patentability dated Feb. 12, 2021 in International application No. PCT/EP2019/081257 in 10 pages.
International Search Report with Written Opinion dated Jan. 10, 2020 in International application No. PCT/EP2019/081257 in 4 pages.
Chou, M. et al. "Ex vivo Expansion of Bovine Corneal Endothelial Cells in Xeno-Free Medium Supplemented with Platelet Releasate", PLOS One, vol. 9, No. 6, p. e99145, Jun. 19, 2014.
Office Action With English Summary Dated Jul. 18, 2023 in Chinese Patent Application No. 201980074865.3 in 12 pgs.
Office Action With English Translation Dated Jul. 18, 2023 in Japanese Patent Application No. 2021-525291 in 15 pgs.

* cited by examiner

Primary Examiner — J. E. Angell
Assistant Examiner — Jacob A Boeckelman
(74) Attorney, Agent, or Firm — KNOBBE, MARTENS, OLSON & BEAR, LLP

(57) ABSTRACT

The present invention relates to the use of a quantity of one or more water-soluble calcium salts and a quantity of glass particles for preparing platelet releasate from a sample of a platelet-rich blood composition obtained from a subject, wherein said quantity of glass particles is from 0.010 g to 0.60 g per ml of said sample and said quantity of the one or more water-soluble calcium salts is from 1.0 μmol to 12.0 μmol per ml of said sample. Systems and methods for preparing a platelet releasate are also disclosed, as well as the platelet releasate obtained therefrom and the use thereof in in vitro and in vivo applications.

17 Claims, 11 Drawing Sheets

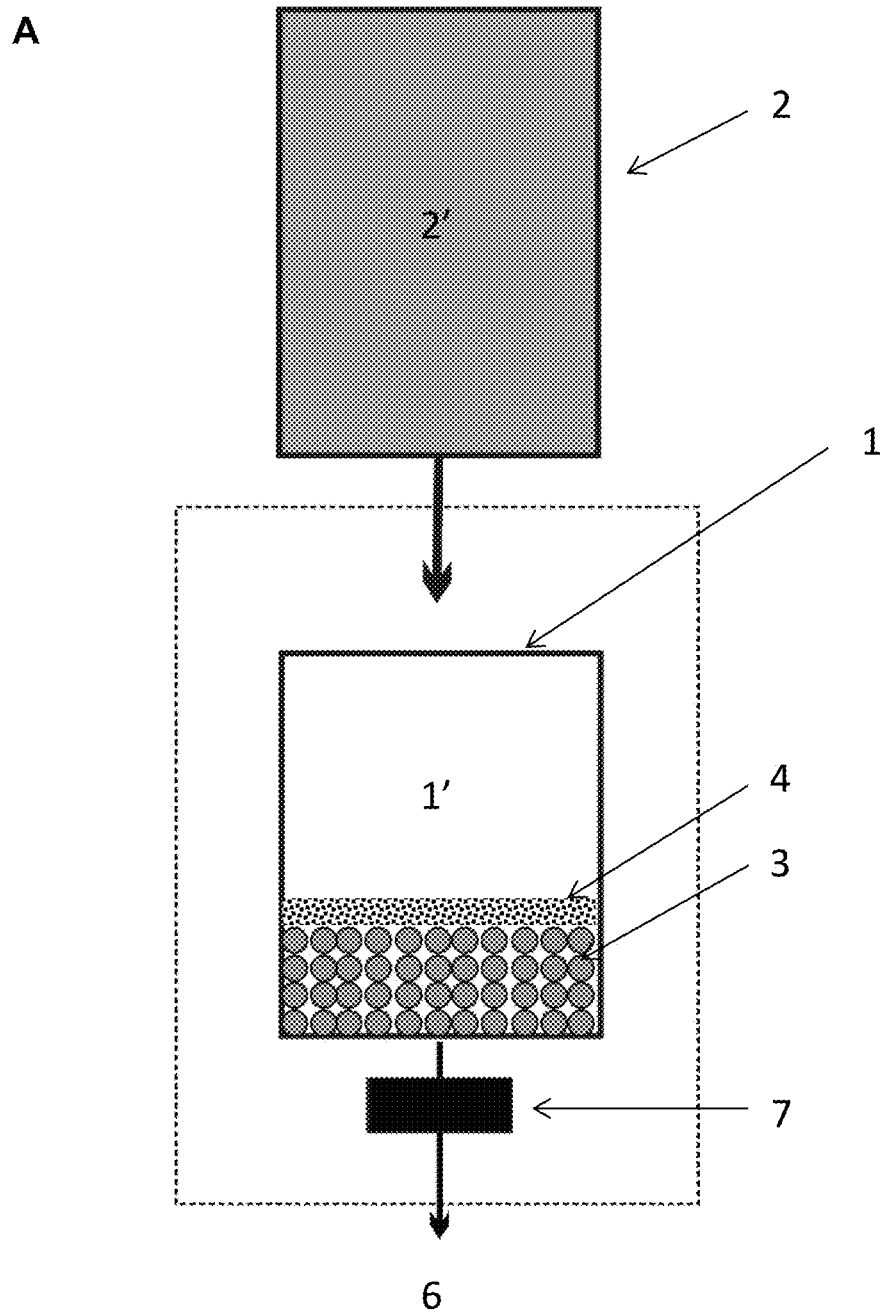

METHODS FOR PREPARING PLATELET RELEASATE

CROSS-REFERENCE TO RELATED APPLICATIONS

This application is a U.S. national phase application under 35 U.S.C. § 371 of International Application No. PCT/EP2019/081257, filed on Nov. 14, 2019, which claims the benefit of European Application No. EP18206107.7, filed Nov. 14, 2018. The content of each of these related applications is incorporated herein by reference in its entirety for all purposes.

FIELD OF THE INVENTION

The invention relates to systems and methods for preparing platelet-derived products and uses of platelet-derived products for preparing platelet-derived products.

BACKGROUND OF THE INVENTION

In specialized laboratories, cells and/or tissues are cultured in growth media. Growth medium is specifically designed to support the growth of cells and comprises besides nutrients and minerals also a complex mixture of (bio)molecules, such as hormones, growth factors and attachment factors. Historically serum, and especially fetal bovine serum (FBS), has been a crucial component of growth media, as a provider of these (bio)molecules as well as numerous low molecular weight nutrients. The emergence of industrial scale mammalian cell culture for the production of protein pharmaceuticals tremendously increased serum consumption. It is estimated that about 800 000 liter of FBS is isolated yearly from more than one million bovine fetuses to meet the demand for serum in cell and/or tissue culture worldwide.

Regenerative medicine, including cell therapy and engineered tissue transplantation, is an emerging field of medicine. In regenerative medicine, human cells or entire tissues are regenerated or replaced to restore or establish normal function. With these advances in medicine, an increased focus on developing safe and contaminant-free culture methods for human cells that are devoid of animal-derived products is required as animal-derived products may cause immune-reactions towards foreign factors as well as cross-species pathogen infections.

In the search for replacing traditionally used FBS as growth supplement in cell culture media, recent research has focused on the application of platelet lysate (PL) that can be produced from platelet concentrate through lysis or platelet releasate (PR) that can be produced from platelet concentrate through platelet activation. PL has been suggested as a viable alternative for FBS in the ex vivo culture of cells for human therapy.

Current methods for preparing platelet-derived products come in two major categories: (i) freeze-thawing (for preparing PL) and (ii) platelet activation (for preparing PR). In the former (i) method a platelet-rich composition is repeatedly subjected to cycles of freezing and thawing. This efficiently lyses platelets, but does not remove fibrinogen leading to coagulation when used as such in culture media. These types of solutions currently require the addition of heparin to prevent coagulation, but heparin in itself is derived from non-human animals nullifying the advantage of using PL over FBS. Furthermore, this method is time consuming and labor intensive. The platelet activation (ii) method is using platelet activators, like thrombin. The use of thrombin however is currently not approved for downstream clinical use in humans. In most cases, the thrombin is non-human (e.g. bovine) in nature as well.

Alternatively, platelets can be activated by addition of at least 15 µmol per ml calcium salts. These will however cause phosphate precipitation in the context of platelet-rich compositions that are supplemented with platelet additive solutions which are often used in blood banks worldwide. Tissue culture is (generally) performed at a constant pH of 7.4 which is maintained by a carbonate buffer system in a humidified and temperature-controlled incubator. At this pH calcium and phosphate have a combined theoretical solubility of 1.7 mM. This implies that when both ions ($Ca^{2+}$) and ($HPO_4^{2-}$) are present in solution at pH 7.4 at a concentration 1.7 mM precipitation is likely to occur. In addition, precipitation is likely to occur faster in solutions containing carbonate ions as well. In the prior art, methods for platelet rich releasate preparation $Ca^{2+}$ is used to activate platelets and the concentration used often results in a final concentration of $Ca^{2+}$ in the eventual culture medium of above 1.7 mM at typical platelet rich releasate fractions 10% (vol/vol). Moreover, when the releasate is prepared from platelet concentrates that are stored in modern platelet additive solutions, also the $HPO_4^{2-}$ concentration will exceed this solubility norm and precipitation will occur. Such calcium complex precipitates stress cells cultured in culture medium comprising PR obtained by the platelet activation (ii) method using at least 15 µmol per ml calcium salts.

In addition, it is desirable to limit the amount of ionized calcium in cell culture media because calcium ions are well known to function in signaling pathways and hence can influence a variety of cellular functions in almost all mammalian cells. Calcium also acts as critical cofactor for many enzymes and is involved in cellular secretion. Extracellular $Ca^{2+}$ concentrations are therefore firmly regulated. Total calcium concentrations in human plasma have a normal range of 2.2-2.6 mM. The element is bound to various plasma proteins, leaving a tightly controlled free ionized $Ca^{2+}$ concentration of 1.1-1.4 mM. These levels are actively maintained within this tight window and rarely fluctuate more than 5% over time (Atchison, D. K. and Beierwltes, W. H. European Journal of Physiology, 2013; 465(1):59-69). Deviations of $Ca^{2+}$ concentration in human physiology lead to hypo- or hypercalcemia and concurrent illness. Consequently, $Ca^{2+}$ concentration in tissue culture media is ideally controlled similarly. For instance, ex vivo culture of chondrocytes requires careful control of $Ca^{2+}$ in order to maintain phenotype (Gigout, A. et al, Osteo Arthritis and Cartilage 2005; 13:1012e1024). This is why commercial suppliers of tissue culture media provide basal media with (e.g. Gibco Cat No 11960) and without (e.g. Gibco Cat No 21068) added $Ca^{2+}$.

Thus, there is a need for new, quick and clinically relevant methods for preparing platelet-derived products.

SUMMARY OF THE INVENTION

As corroborated by the experimental section, which illustrates certain representative embodiments of the invention, the inventors found that a platelet releasate or lysate can be prepared from a sample of a platelet-rich blood composition obtained from a subject, such as expired human platelet concentrate, using from 0.010 g to 0.60 g glass particles per ml of said sample and from 1.0 µmol to 12.0 µmol of one or more water-soluble calcium salts per ml of said sample. The presently claimed method provides a means to maximally lower final $Ca^{2+}$ concentration. We have calculated that a final $Ca^{2+}$ concentration of about 0.8 mM in total (100%) platelet releasate allows to remain below the solubility of calcium phosphate when used at 10% (vol/vol) fraction in a typical culture medium.

Additionally, the present inventors have developed a closed, sterile, system for preparing a platelet releasate or platelet lysate. Furthermore, the present inventors have found that the platelet releasate obtained thereby can be used in cell culture or tissue culture as a replacer for serum additives such as fetal bovine serum (FBS). The platelet releasates as taught herein were found not to induce precipitations in the growth medium. Additionally, the platelet releasates or lysates as taught herein can also be used in the treatment of hard- and soft-tissue injuries, inflammatory diseases, bone diseases, degenerative joint diseases, degenerative disc diseases, skin conditions, alopecia areata, endometrial disease, vaginal atrophy, ocular surface diseases, carpal tunnel syndrome, neurodegenerative disorders, peripheral arterial disease and pain and for improving the appearance of the skin and/or hair.

The invention therefore provides the following aspects:

Aspect 1. Use of a quantity of one or more water-soluble calcium salts and a quantity of glass particles for preparing platelet releasate from a sample of a platelet-rich blood composition obtained from a subject, wherein said quantity of glass particles is from 0.010 g per ml to 0.60 g per ml of said sample and said quantity of the one or more water-soluble calcium salts is from 1.0 µmol per ml to 12.0 µmol per ml of said sample.

Aspect 2. A system for preparing a platelet releasate comprising
a first container (1) having a first containing space (1') wherein said first containing space (1')
is configured to receive a quantity ($Q_{bc}$) of a platelet-rich blood composition comprised in a second containing space (2') of a second container (2);
holds a quantity ($Q_{gp}$) of glass particles (3); and
holds a quantity ($Q_{cc}$) of one or more water-soluble calcium salts (4) or is configured to receive a quantity ($Q_{cc}$) of one or more water-soluble calcium salts (4) held by a third containing space (5') of a third container (5);
wherein the ratio $Q_{gp}:Q_{bc}$ is from 0.010 to 0.60 g per ml of said sample and the ratio $Q_{cc}:Q_{bc}$ is from 1.0 to 12.0 µmol per ml of said sample.

Aspect 3. The system according to aspect 2, further comprising a first tube of which the proximal end is held by a first opening in the first containing space (1') and the distal end is held by an opening in the third containing space (5'), wherein the tube is configured to connect the first container (1) to the third container (5) and to place the first containing space (1') in fluid communication with the third containing space (5').

Aspect 4. The system according to aspect 3, wherein the first tube comprises means for reversibly interrupting the fluid communication between the first containing space (1') and the third containing space (5'), preferably wherein said means are an external clamp or a valve.

Aspect 5. The system according to any one of aspects 2 to 4, wherein the first containing space (1') further comprises
a second opening configured to connect to an opening of the second containing space (2') of a second container (2); and
a third opening configured to connect to an opening of a fourth containing space of a fourth container, wherein the fourth containing space is configured to receive and/or hold the platelet releasate prepared using the system.

Aspect 6. The system according to aspect 5, further comprising
a second tube of which the proximal end is held by the second opening in the first containing space (1') and the distal end is connectable to the second containing space (2'), wherein the second tube is configured to connect the first container (1) to the second container (2) and to place the first containing space (1') in fluid communication with the second containing space (2');
a third tube of which the proximal end is held by the third opening in the first containing space (1') and the distal end is connectable to a fourth containing space of a fourth container, wherein the tube is configured to connect the first container (1) with the fourth container, and to place the first containing space (1') in fluid communication with the fourth containing space; and
optionally filtering means (7) which are located between the third opening in the first containing space (1') and the fourth containing space.

Aspect 7. The system according to aspect 6, wherein the distal end of the second tube is connectable to the second containing space (2') and/or the distal end of the third tube is connectable to the fourth containing space by welding.

Aspect 8. The system according to any one of aspects 2 to 7, wherein the ratio $Q_{gp}:Q_{bc}$ is from 0.10 to 0.40 g per ml of said sample and the ratio $Q_{cc}:Q_{bc}$ is from 3.0 to 8.0 µmol per ml of said sample.

Aspect 9. Use of the system according to any one of aspects 2 to 8, for producing platelet releasate or platelet lysate.

Aspect 10. A method for preparing platelet releasate from a sample of a platelet-rich blood composition obtained from a subject comprising the steps of:
a) contacting said sample with from 0.010 g to 0.60 g of glass particles per ml of said sample and from 1.0 µmol to 12.0 µmol of one or more water-soluble calcium salts per ml of said sample thereby obtaining a mixture;
b) allowing the mixture obtained in step a) to coagulate thereby obtaining a coagulum and platelet releasate; and
c) recovering the platelet releasate obtained in step b) from the mixture.

Aspect 11. The use according to aspect 1 or the method according to aspect 10, wherein said sample is contacted with from 0.10 g to 0.40 g of glass particles per ml of said sample and from 3.0 µmol to 8.0 µmol of one or more water-soluble calcium salts per ml of said sample.

Aspect 12. The use according to aspect 1, the system according to any one of aspects 2 to 8, or the method according to aspect 10 or 11, wherein said glass particles have an average diameter from 1.0 mm to 5.0 mm, preferably from 2.0 mm to 4.0 mm.

Aspect 13. The use according to any one of aspects 1, 11 or 12, the system according to any one of aspects 2 to 8 or 12, or the method according to any one of aspects 10 to 12, wherein said glass particles are silica-based glass particles, preferably soda-lime-silica or soda-lime glass particles, sodium borosilicate glass particles, aluminosilicate glass particles, lead-oxide glass particles or fused-silica glass particles.

Aspect 14. The use according to any one of aspects 1 or 11 to 13, the system according to any one of aspects 2 to 8, 12 or 13, or the method according to any one of aspects 10 to 13, wherein said one or more water-soluble calcium salts are selected from the group consisting of calcium chloride, calcium hydroxide, calcium acetate, calcium carbonate, calcium bicarbonate, calcium chlorate, calcium perchlorate, calcium sulfate, calcium nitrate, calcium nitrite, calcium lactate, calcium glubionate, calcium gluceptate and calcium gluconate or mixtures thereof, preferably calcium chloride.

Aspect 15. The method according to any one of aspects 10 to 14, wherein in step c) said platelet releasate obtained in step b) is recovered from the mixture by passing the mixture through at least one filter.

Aspect 16. The method according to any one of aspects 10 to 15, wherein in step b) said mixture is allowed to coagulate for a period from 1 hour to 20 hours, preferably for a period from 2 to 6 hours, more preferably for a period from 2 to 4 hours.

Aspect 17. The use according to any one of aspects 1 or 11 to 14 or the method according to any one of aspects 10 to 16, wherein said platelet-rich blood composition is selected from platelet concentrate, plasma and whole blood, preferably platelet concentrate.

Aspect 18. The method according to any one of aspects 10 to 17, further comprising a step of lysing the platelets present in the obtained coagulum and/or platelet releasate obtained in step b) thereby obtaining a platelet lysate.

Aspect 19. A platelet releasate obtained by the method according to any one of aspects 10 to 17, preferably wherein such a releasate has a final calcium ion concentration (Ca') of below 0.8 mM in total (100%) platelet releasate.

Aspect 20. A platelet lysate obtained by the method according to aspect 18, preferably wherein such a releasate has a final calcium ion concentration (Ca') of below 0.8 mM in total (100%) platelet releasate.

Aspect 21. A pharmaceutical composition comprising the platelet releasate according to aspect 19 or the platelet lysate according to aspect 20.

Aspect 22. A cosmetic composition comprising the platelet releasate according to aspect 19 or the platelet lysate according to aspect 20.

Aspect 23. A composition comprising a platelet-rich blood composition, from 1.0 mM to 12.0 mM of $Ca^{2+}$ ions in addition to the $Ca^{2+}$ ions present in the platelet-rich blood composition and from 0.010 g to 0.60 g of glass particles per ml of said platelet-rich blood composition.

Aspect 24. A container comprising the composition according to aspect 23.

Aspect 25. The platelet releasate according to aspect 19, the platelet lysate according to aspect 20 or the pharmaceutical composition according to aspect 21 for use in medicine.

Aspect 26. The platelet releasate according to aspect 19, the platelet lysate according to aspect 20 or the pharmaceutical composition according to aspect 21 for use in the treatment of hard- and soft-tissue injuries, inflammatory diseases, bone diseases, degenerative joint diseases, degenerative disc diseases, skin conditions, alopecia areata, endometrial disease, vaginal atrophy, ocular surface diseases, carpal tunnel syndrome, neurodegenerative disorders, peripheral arterial disease and pain comprising administering to a subject an effective amount of the platelet releasate, the platelet lysate or the pharmaceutical composition.

Aspect 27. Use of the platelet releasate according to aspect 19, the platelet lysate according to aspect 20 or the cosmetic composition according to aspect 22 for improving the appearance of the skin and/or hair.

Aspect 28. Use of the platelet releasate according to aspect 19 or the platelet lysate according to aspect 20 in cell culture or tissue culture.

These and further aspects and preferred embodiments of the invention are described in the following sections and in the appended claims. The subject-matter of the appended claims is hereby specifically incorporated in this specification.

(v/v). 'Standard' hPR was produced by two freeze-thaw cycles with subsequent centrifugation, 'CaCl$_2$+glass' hPR was prepared with 5 mM CaCl$_2$ and 0.2 g soda-lime glass beads per mL of PC. Three commercial competitors were included, FBS was included as gold standard.

Figures 10, 11:
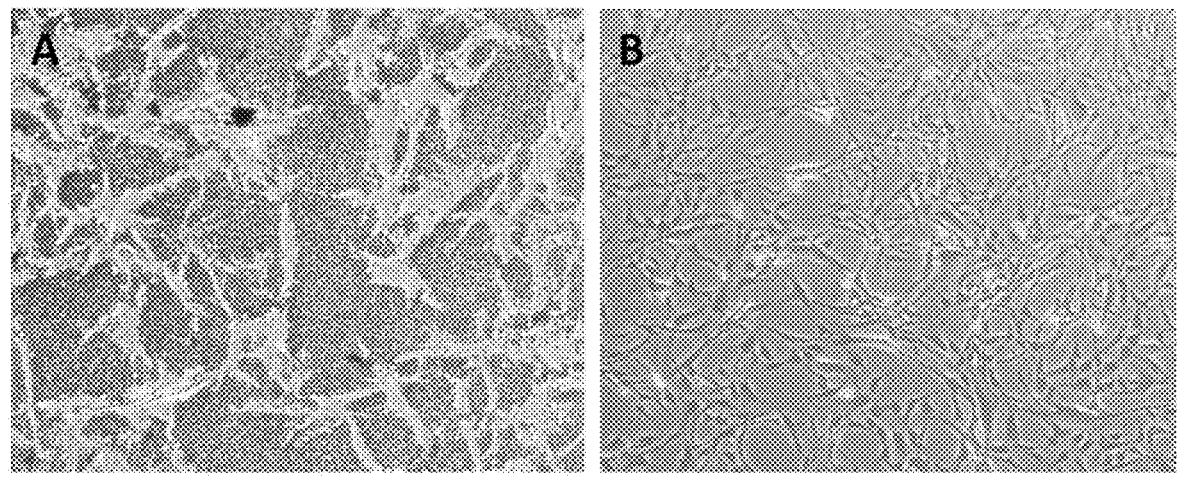

FIG. 10. Microscopic images of MSC cultured in DMEM growth medium supplemented with (A) 10% (v/v) hPR prepared with 15 mM CaCl$_2$ without glass beads and (B) 10% (v/v) hPL prepared with 4 mM CaCl$_2$ and 0.20 g glass beads per ml PC.

FIG. 11. Schematic overview of experimental conditions and results of example 8. In the upper row the different concentrations of CaCl$_2$ are indicated, while in the left column the different weights and concentrations of glass particles are indicated. The absence of retraction in less than 3 h is indicated by an 'X', while successful retraction in less than 3 h is indicated by a 'V'.

Figure 12:
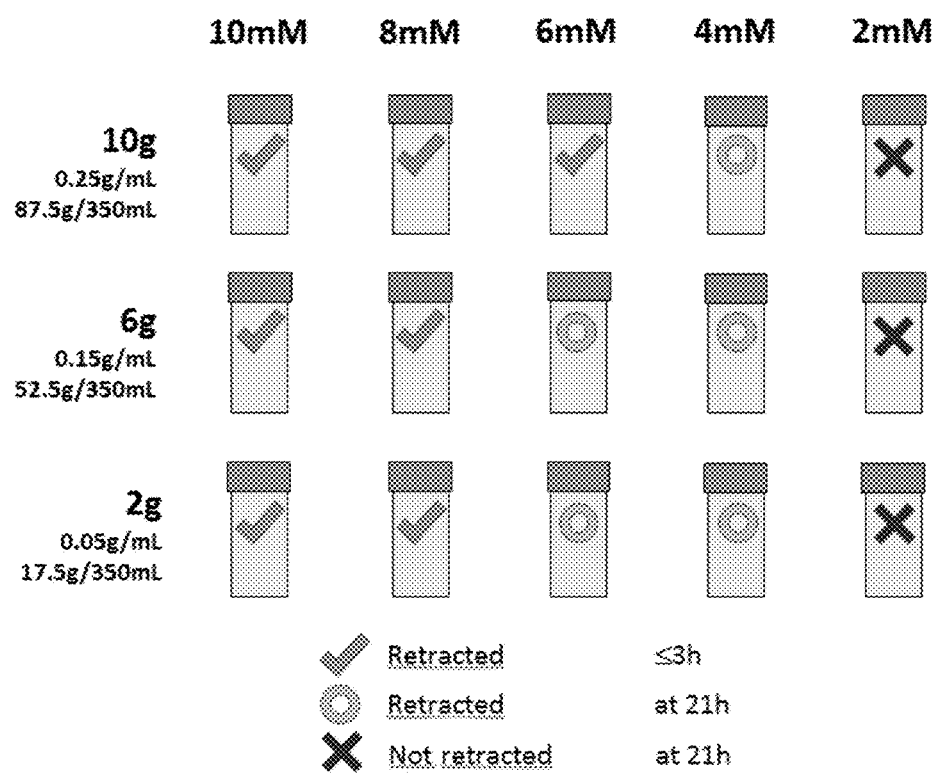

FIG. 12. Schematic overview of experimental conditions and results of example 9. In the upper row the different concentrations of CaCl$_2$) are indicated, while in the left column the different weights and concentrations of glass particles are indicated. The absence of retraction is indicated by an 'X', while successful retraction in less than 3 h is indicated by a 'V'. An open circle indicates clot retraction between 3 h and 21 h.

Figure 13:
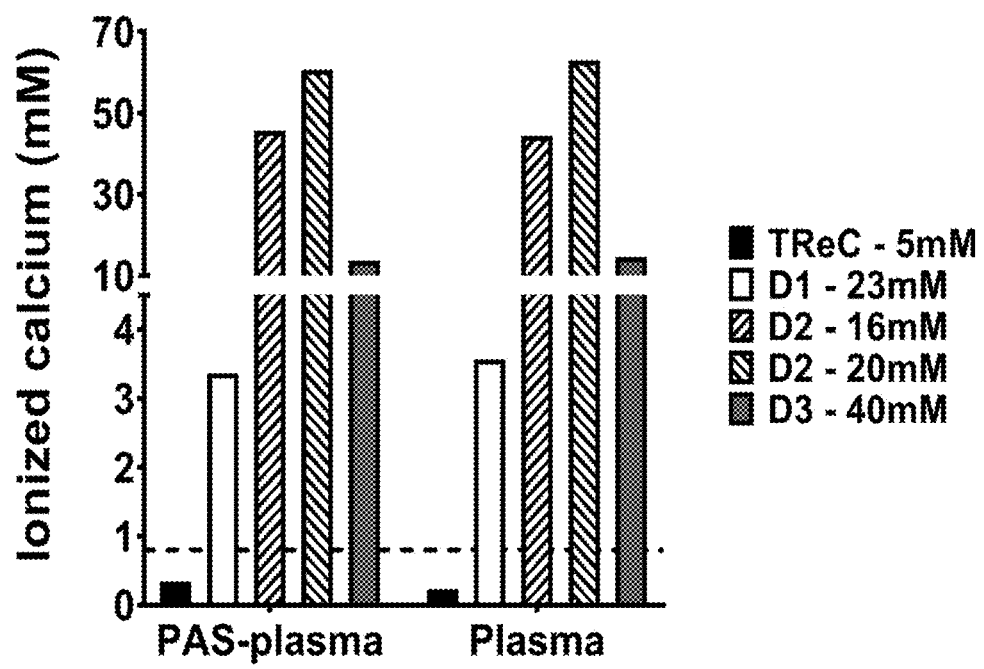

FIG. 13. Concentration of Ca$^{2+}$ (ionized calcium) in platelet releasates prepared according to cited prior art. In a paired experiment platelet concentrates in additive solution (PAS-plasma) or in pure plasma (Plasma) were treated with the claimed method (TReC) or those from prior art documents.

Figure 14:
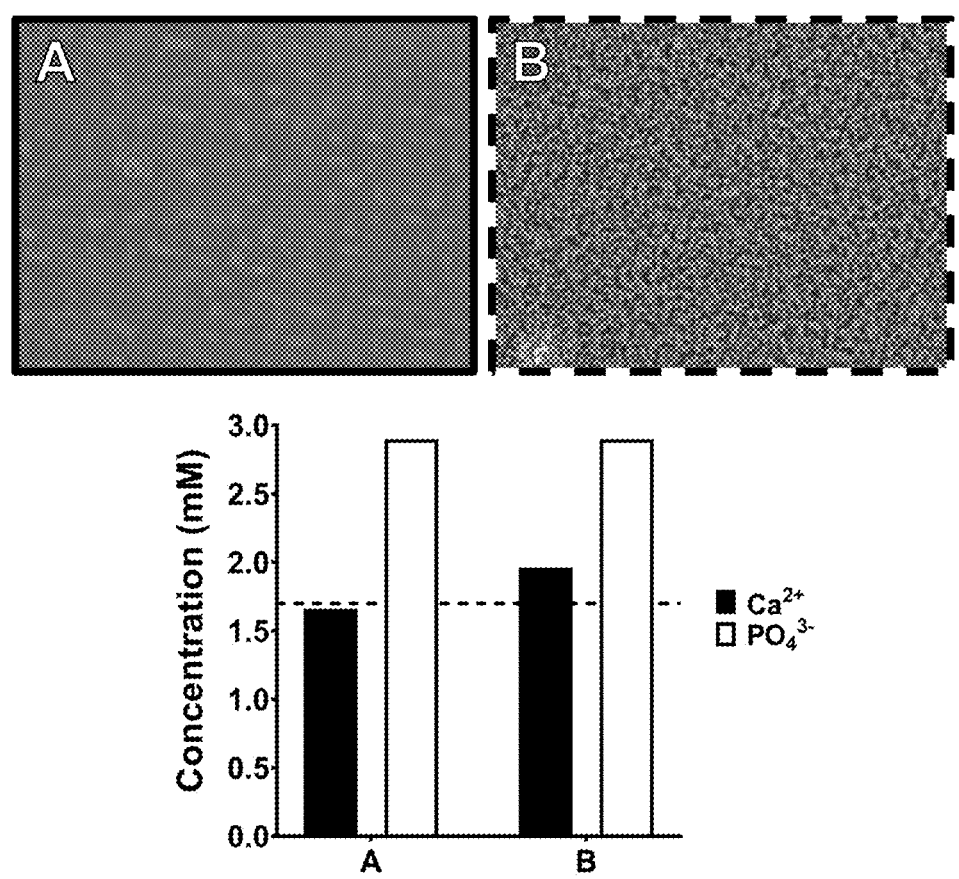

FIG. 14. Precipitation of chemical phosphate (PO$_4^{3-}$) complexes with calcium (Ca$^{2+}$) in tissue culture media.

DETAILED DESCRIPTION OF THE INVENTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of ±10% or less, preferably ±5% or less, more preferably ±1% or less, and still more preferably ±0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any 3 or more, 4 or more, 5 or more, 6 or more, or 7 or more etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

As corroborated by the experimental section, which illustrates certain representative embodiments of the invention, the inventors found that a platelet releasate can be prepared from a sample of a platelet-rich blood composition obtained from a subject, such as expired human platelet concentrate, using from 0.010 g to 0.60 g glass particles per ml of said sample and from 1.0 μmol to 12.0 μmol of one or more water-soluble calcium salts per ml of said sample. Furthermore, the present inventors have found that the platelet releasate obtained thereby can be used in cell culture or tissue culture as a replacer for serum additives such as fetal bovine serum (FBS). The platelet releasates as taught herein were found not to induce precipitations in the growth medium. Additionally, the platelet releasates as taught herein can also be used in the treatment of hard- and soft-tissue injuries, inflammatory diseases, bone diseases, degenerative joint diseases, degenerative disc diseases, skin conditions, alopecia areata, endometrial disease, vaginal atrophy, ocular surface diseases, carpal tunnel syndrome, neurodegenerative disorders, peripheral arterial disease and pain and for improving the appearance of the skin and/or hair.

Accordingly, a first aspect provides the use of a quantity of one or more soluble calcium salts and a quantity of glass particles for preparing platelet releasate from a sample of a platelet-rich blood composition obtained from a subject, wherein said quantity of glass particles is from 0.010 g to 0.60 g per ml of said sample and said quantity of the one or more water-soluble calcium salts is from 1.0 µmol to 12.0 µmol per ml of said sample.

The term "platelet releasate" or "platelet secretome" as used herein refers to a solution comprising the granular and exosomal contents secreted by one or more activated platelets. Non-limiting examples of the granular and exosomal contents include coagulation factors, small molecules, energy equivalents, chemokines, cytokines, adhesion molecules, hormones, immunologic molecules and regulators of growth (or growth factors), cell division, apoptosis and/or angiogenesis, and attachment factors. In particular embodiments, the term does not encompass platelet lysate. The term "platelet lysate" as used herein refers to a solution comprising the content of one or more lysed platelets. The term may also encompass platelet releasate. Methods for obtaining platelet lysate are known in the art and comprises freeze-thawing of platelets.

Preferably, the platelet releasate or the platelet lysate is substantially free of cells (i.e. at most 50 000 cells per µl of platelet releasate or lysate, preferably at most 40 000 cells per µl of platelet releasate or lysate). The term "cell" as used herein does not encompass extracellular vesicles.

Except when noted, the terms "subject" or "patient" can be used interchangeably and refer to animals, preferably warm-blooded animals, more preferably vertebrates, even more preferably mammals such as chimpanzees and other apes and monkey species, cattle, sheep, pigs, goats, horses, dogs, cats, mice, rats, guinea pigs, and the like, still more preferably primates, and specifically includes human patients and non-human mammals and primates. Preferred subjects are human subjects. The terms "subject" or "patient" include subjects in need of treatment, more particularly subjects that would benefit from treatment of a given condition, particularly hard- and soft-tissue injuries, inflammatory diseases, bone diseases, degenerative joint diseases, degenerative disc diseases, skin conditions, alopecia areata, endometrial disease, vaginal atrophy, ocular surface diseases, carpal tunnel syndrome, neurodegenerative disorders, peripheral arterial disease and pain. Such subjects may include, without limitation, those that have been diagnosed with said condition, those prone to develop said condition and/or those in who said condition is to be prevented. The terms "subject" or "patient" include subjects in need of improved appearance of the skin and/or hair. The term "subject" or "patient" includes both singular and plural form subjects or patients unless the context clearly dictates otherwise.

The term "platelet-rich blood composition" as used herein refers to a composition derived from whole blood comprising at least 50 000, preferably at least 600 000 platelets per µl or at least 800 000 platelets per Non-limiting examples of platelet-rich blood compositions are platelet concentrate (such as buffy coat derived platelet concentrate, apheresis-platelet concentrate or platelet-rich plasma derived platelet concentrate), whole blood, blood plasma and platelet-rich plasma. Methods for obtaining platelet concentrate, blood plasma or platelet-rich plasma from whole blood are known in the art and include differential centrifugation and methods as described in Hardwick J., Blood processing. 2008. 3(20): 148-176, and especially p. 164 to 175, including apheresis, pooling of buffy coats or platelet-rich plasma production.

Preferably, the platelet-rich blood composition comprises substantially no (e.g. less than 10 white blood cells per preferably less than 5 white blood cells per µl) white blood cells and/or less than 4 000 red blood cells per µl.

The terms "sample" or "biological sample" as used throughout this specification in reference to a platelet-rich blood composition obtained (isolated, removed) from a subject encompasses samples of a platelet-rich blood composition directly or indirectly obtained (isolated, removed) from the subject.

Indirectly obtained samples of a platelet-rich blood composition include samples obtained by processing whole blood, which can be directly obtained from the subject, in order to arrive at a platelet-rich blood composition, such as by apheresis or centrifugation. Preferably, a sample may be readily obtainable by minimally invasive methods, such as blood collection ('liquid biopsy'), allowing the provision/removal/isolation of the sample from a subject.

In particular embodiments, the sample is a pooled sample, meaning that the sample is taken from a single pool of samples, wherein the pool of samples comprises samples of two or more subjects and/or samples from a single subject taken at different time points.

In particular embodiments, the sample has a volume from 5.0 ml to 50 000.0 ml, from 10.0 ml to 10 000.0 ml, from 10.0 ml to 5 000.0 ml, from 10.0 ml to 2 500.0 ml, from 10.0 ml to 1 000.0 ml, from 50.0 ml to 750.0 ml, from 50.0 ml to 500.0 ml, from 100.0 ml to 500.0 ml, from 150.0 ml to 450.0 ml, preferably from 100.0 to 500.0 ml.

The term "platelet concentrate" as used herein refers to a platelet-rich blood composition comprising at least 50 000 platelets per µl, preferably at least 600 000 platelets per µl or at least 800 000 platelets per µl, and plasma and/or one or more platelet additive solution(s) (e.g. storage solution for platelets (SSP+)). The platelet additive solution can be used to replace part (e.g. from 5.0 to 95.0% (v/v)) of the plasma. Platelet concentrate may be prepared by any methods known in the art for preparing platelet concentrate such as described in Hardwick J., Blood processing. 2008. 3(20):148-176, and especially p. 164 to 175, including apheresis, pooling of buffy coats or platelet-rich plasma production. Accordingly, the term "platelet concentrate" also encompasses platelet-rich plasma, such as concentrated platelet-rich plasma, which typically does not comprise a platelet additive solution.

Preferably, the platelet concentrate comprises substantially no (e.g. less than 10 white blood cells per µl, preferably less than 5 white blood cells per µl) white blood cells.

In particular embodiments, the platelet-rich blood composition comprises at least 50 000 platelets per µl, at least 100 000 platelets per µl, at least 200 000 platelets per µl, at least 300 000 platelets per µl, at least 400 000 platelets per µl, at least 500 000 platelets per µl, at least 600 000 platelets per µl, at least 700 000 platelets per µl, at least 800 000 platelets per µl, at least 900 000 platelets per µl or at least 1 000 000 platelets per µl, preferably at least 600 000 platelets per µl or at least 800 000 platelets per A. For example, from 800 000 to 1 200 000 platelets per µl., the platelet-rich blood composition may comprise from 100 000 to 3 000 000 platelets per µl, from 200 000 to 2 000 000 platelets per µl, or from 200 000 to 1 500 000 platelets per µl, preferably from 200 000 to 2 000 000 platelets per µl, more preferably from 800 000 to 1 200 000 platelets per µl.

In particular embodiments, the platelet-rich blood composition comprises at least 5.0% (v/v), at least 10.0% (v/v), at least 15.0% (v/v), at least 20.0% (v/v), at least 25.0% (v/v), at least 30.0% (v/v), at least 35.0% (v/v), at least 40.0% (v/v), at least 45.0% (v/v), at least 50.0% (v/v), at least 55.0% (v/v), at least 60.0% (v/v), at least 65.0% (v/v), at least 70.0% (v/v), at least 75.0% (v/v) or at least 85.0% (v/v), preferably at least 30.0% (v/v) of plasma. Plasma typically comprises one or more coagulation factors such as coagulation Factor I, Factor II, Factor III, Factor IV, Factor V, Factor VI, Factor VII, Factor VIII, Factor IX, Factor X, Factor XI, Factor XII and/or Factor XIII. Preferably, the one or more coagulation factors are present in the plasma in normal physiological levels (i.e. physiological concentration of said one or more coagulation factors in healthy subjects).

In particular embodiments, the platelet-rich blood composition is selected from platelet concentrate, plasma (such as platelet-rich plasma) and whole blood. In more particular embodiments, the platelet-rich blood composition is platelet concentrate or platelet-rich plasma, preferably platelet concentrate.

In particular embodiments, the platelet concentrate comprises at least 600 000 platelets per µl, at least 700 000 platelets per µl, at least 800 000 platelets per µl, at least 900 000 platelets per µl or at least 1 000 000 platelets per µl, preferably at least 1 000 000 platelets per µl.

In particular embodiments, the platelet concentrate comprises from 600 000 to 3 000 000 platelets per µl, from 700 000 to 2 500 000 platelets per µl, from 800 000 to 2 000 000 platelets per µl or from 800 000 to 1 500 000 platelets per µl.

In particular embodiments, the platelet concentrate is a platelet concentrate obtained by apheresis or buffy-coat. In particular embodiments, the platelet concentrate is platelet concentrate prepared and approved for medical use in transfusion e.g. by a medical doctor or other clinician such as a nurse.

The term "platelet additive solution" or "PAS" as used herein refers to an electrolyte solution for the preservation of platelets. Platelet additive solutions typically comprise acetate and optionally potassium, magnesium and/or phosphate. Platelet additive solution may extend the platelet shelf life, reduce platelet activation, improve functionality of platelets, maintain pH and reduce allergic reactions. The platelet additive solution may be any platelet additive solution known in the art, for example such as described in Table 1 of Tynngard et al. Preparation, storage and quality control of platelet concentrates. 2009. Transfusion and Apheresis Science. 41:97-104. Non-limiting examples of PAS include PAS-B (i.e. comprising acetate), PAS-C (i.e. comprising acetate and phosphate), PAS-F (i.e. comprising acetate, magnesium and potassium as key constituents), PAS-E (i.e. comprising acetate, magnesium, potassium and phosphate) or combinations thereof.

In particular embodiments, the platelet concentrate comprises at least 5.0% (v/v), at least 10.0% (v/v), at least 15.0% (v/v), at least 20.0% (v/v), at least 25.0% (v/v), at least 30.0% (v/v), at least 35.0% (v/v), at least 40.0% (v/v), at least 45.0% (v/v), at least 50.0% (v/v), at least 55.0% (v/v), at least 60.0% (v/v), at least 65.0% (v/v), at least 70.0% (v/v), at least 75.0% (v/v) or at least 85.0% (v/v), preferably at least 60.0% (v/v) of one or more platelet additive solution(s).

In particular embodiments, the platelet concentrate comprises from 0.0 to 95.0% (v/v), from 5.0 to 95.0% (v/v), from 10.0 to 90.0% (v/v), from 20.0 to 80.0% (v/v), from 30.0 to 80.0% (v/v), from 40.0 to 80.0% (v/v), from 50.0 to 80.0% (v/v), from 60 to 80.0% (v/v) or from 65.0 to 75.0% (v/v), preferably from 60.0 to 90.0% (v/v), of one or more platelet additive solution(s).

In more particular embodiments, the platelet additive solution is a PAS-E solution and comprises at least 32.50 mM acetate, at least 5.0 mM potassium, at least 1.50 mM magnesium and at least 28.20 mM phosphate.

In more particular embodiments, the platelet additive solution is comprises $Na_3$-citrate $2H_2O$, Na-acetate $3H_2O$, NaCl and optionally $NaH_2PO_4$ $2H_2O$, $Na_2HPO_4$, KCl and/or $MgCl_2$ $6H_2O$.

In even more particular embodiments, the platelet additive solution is a PAS-E solution and comprises:
- from 2.0 to 4.0 g/L, preferably from 2.90 to 3.20 g/L, $Na_3$-citrate $2H_2O$,
- from 3.0 to 5.0 g/L, preferably from 4.0 to 4.50 g/L, Na-acetate $3H_2O$,
- from 3.0 to 8.0 g/L, preferably from 4.0 to 7.0 g/L, NaCl, and optionally
- from 9.0 to 1.20 g/L, preferably from 1.0 to 1.10 g/L, $NaH_2PO_4$ $2H_2O$,
- from 2.90 to 3.20, preferably from 3.0 to 3.10 g/L, $Na_2HPO_4$,
- from 0.30 to 0.45 g/L, preferably from 0.350 to 0.40 g/L KCl, and/or
- from 0.250 to 0.350 g/L, preferably from 0.290 to 0.310 g/L $MgCl_2$ $6H_2O$.

For example, the platelet additive solution is SSP+(Macopharma) or T-PAS+(TerumoBCT, Inc.).

In particular embodiments, the platelet-rich blood composition comprises at least 700 000 platelets per µl and from 60.0 to 90.0% (v/v), of one or more platelet additive solution(s).

In particular embodiments, the platelet-rich blood composition is submitted to pathogen inactivation (also known as pathogen reduction). Pathogen inactivation of whole blood or blood-derived products is known in the art and may be performed using the Intercept Blood System (CERUS, Concord CA), Mirasol Pathogen Reduction (Terumo BCT, Denver, CO) or Theraflex UVC (Macopharma, Tourcoing, FR).

In particular embodiments, the platelet-rich blood composition is substantially free of any infectious agent (e.g. microorganism including bacteria, viruses and protozoa) which may cause a disease in a subject to whom the platelet-rich blood composition or a derivative thereof is administered. In more particular embodiments, the platelet-rich blood composition is substantially free of human immunodeficiency virus (HIV), hepatitis (e.g. hepatitis B or hepatitis C) virus and *Treponema pallidum* (i.e. bacterium causing syphilis).

Platelet concentrate has a short shelf-life (e.g. 5-7 days) and as a result many donors are needed to maintain the minimum supply of platelet concentrate for transfusion at any given time. Because of short shelf-life and varying demand and supply of platelet concentrate, it is difficult for the blood banks to manage platelet concentrate stock. As a result hereof, 3-5% of the donated platelet concentrate expires (i.e. is no longer considered safe for human transfusion) before it can be used for transfusion and hence is discarded as biohazardous waste. The shelf life of platelet concentrate is kept short because of increased risk of pathogen outgrowth during storage at room temperature. Besides this, platelet function declines during storage, also known as the platelet storage lesion. Platelet concentrate is an expensive product, so the financial costs of discarding expired platelet concentrate are high. Present inventors found that expired platelet concentrate could be used to prepare platelet releasate by the methods as taught herein. In particular embodiments, the methods as taught herein optionally comprise lysing the platelets present in the platelet-rich blood composition obtaining a platelet lysate. If such a lysing step is present, the method as taught herein will be a method for preparing a platelet lysate and a platelet lysate is obtained from said platelet releasate. The inventors have further found that said platelet releasate or platelet lysate can be used in cell culture, in the treatment of hard- and soft-tissue injuries, inflammatory diseases, bone diseases, degenerative joint diseases, degenerative disc diseases, skin conditions, alopecia areata, endometrial disease, vaginal atrophy, ocular surface diseases, carpal tunnel syndrome, neurodegenerative disorders, peripheral arterial disease and pain and for improving the appearance of the skin and/or hair.

In particular embodiments, the platelet concentrate is expired platelet concentrate.

The term "expired" as used herein with reference to platelet concentrate denotes platelet concentrate which is no longer considered suitable for transfusion. The expiration time and/or expiration conditions for platelet concentrate may be different from jurisdiction to jurisdiction. For example, the platelet concentrate may be considered expired at least 3 days post donation, at least 4 days post donation, at least 5 days post donation, at least 6 days post donation, at least 7 days post donation, at least 8 days post donation, at least 9 days post donation, at least 10 days post donation, at least 11 days post donation, at least 12 days post donation, at least 13 days post donation, at least 14 days post donation or at least 15 days post donation, preferably at least 10 days post donation.

In particular embodiments, the platelet concentrate is used at least 5 days, preferably at least 10 days, after the platelet concentrate is obtained from the subject.

The term "water-soluble calcium salt" as used herein refers to a calcium salt or a calcium complex having a solubility of at least 0.010 g per 100 ml of water, preferably when measured at atmospheric pressure of 1 atm, at a temperature of 20.0° C. and at a pH of 7.4. Preferably, the water is distilled water. Non-limiting examples of water-soluble calcium salts are calcium chloride, calcium hydroxide, calcium acetate, calcium carbonate, calcium bicarbonate, calcium chlorate, calcium perchlorate, calcium sulfate, calcium nitrate, calcium nitrite, calcium lactate, calcium glubionate, calcium gluceptate and calcium gluconate. Non-limiting examples of calcium complexes include calcium ethylenediaminetetraacetic acid (EDTA) and calcium pentetic acid or diethylene triamine pentaacetic acid (DTPA) and the like.

In particular embodiments, the one or more water-soluble calcium salts are selected from the group consisting of calcium chloride, calcium hydroxide, calcium acetate, calcium carbonate, calcium bicarbonate, calcium chlorate, calcium perchlorate, calcium sulfate, calcium nitrate, calcium nitrite, calcium lactate, calcium glubionate, calcium gluceptate, and calcium gluconate, or mixtures thereof. In a preferred embodiment, the water-soluble calcium salt is calcium chloride. The term "calcium chloride" or "$CaCl_2$" as used herein refers to calcium chloride with CAS-nummer 10043-52-4.

In particular embodiments, the one or more water-soluble calcium salts are non-toxic in vivo. In more particular embodiments, the one or more water-soluble calcium salts do not comprise calcium bromide. In particular embodiments, the quantity of the one or more water-soluble calcium salts is from 0.010 µmol to 20.0 µmol, from 0.050 µmol to 20.0 µmol, from 0.10 µmol to 15.0 µmol, from 0.050 µmol to 12.0 µmol, from 1.0 µmol to 12.0 µmol, from 0.050 µmol to 10.0 µmol, from 0.50 µmol to 10.0 µmol, from 1.0 µmol to 10.0 µmol, from 1.0 µmol to 9.0 µmol, from 1.0 µmol to 8.0 µmol, from 1.0 µmol to 7.0 µmol, from 1.0 µmol to 6.0 µmol, from 2.0 µmol to 12.0 µmol, from 2.0 µmol to 10.0 µmol, from 2.0 µmol to 9.0 µmol, from 0.050 µmol to 8.0 µmol, from 2.0 µmol to 8.0 µmol, from 3.0 µmol to 8.0 µmol, from 2.0 µmol to 7.0 µmol, from 3.0 µmol to 7.0 µmol, from 2.0 µmol to 6.0 µmol or from 3.0 µmol to 6.0 µmol per ml of the sample, preferably from 1.0 µmol to 12.0 µmol or from 2.0 µmol to 10.0 µmol per ml of the sample, more preferably from 3.0 µmol to 8.0 µmol per ml of the sample. For example, 4.0 µmol or 5.0 µmol per ml of the sample. The quantity of the one or more water-soluble calcium salts typically refers to the quantity of exogenously added one or more water-soluble calcium salts, and not to those already present in the platelet-rich blood composition.

In particular embodiments, the quantity of the one or more water-soluble calcium salts is from 0.010 mM to 20.0 mM, from 0.050 mM to 20.0 mM, from 0.10 mM to 15.0 mM, from 0.050 mM to 12.0 mM, from 1.0 mM to 12.0 mM, from 0.050 mM to 10.0 mM, from 0.50 mM to 10.0 mM, from 1.0 mM to 10.0 mM, from 1.0 mM to 9.0 mM, from 1.0 mM to 8.0 mM, from 1.0 mM to 7.0 mM, from 1.0 mM to 6.0 mM, from 2.0 mM to 12.0 mM, from 2.0 mM to 10.0 mM, from 2.0 mM to 9.0 mM, from 0.050 mM to 8.0 mM, from 2.0 mM to 8.0 mM, from 3.0 mM to 8.0 mM, from 2.0 mM to 7.0 mM, from 3.0 mM to 7.0 mM, from 2.0 mM to 6.0 mM or from 3.0 mM to 6.0 mM, preferably from 1.0 mM to 12.0 mM or from 2.0 mM to 10.0 mM, more preferably from 3.0 mM to 8.0 mM. For example, 4.0 mM or 5.0 mM.

In particular embodiments, the one or more water-soluble calcium salts are dissolved in water, preferably distilled water, prior to adding the one or more water-soluble calcium salts to the platelet-rich blood composition. In particular embodiments, the volume of water in which the one or more water-soluble calcium salts are dissolved is at most 5.0% (v/v), at most 4.0% (v/v), at most 3.0% (v/v), at most 2.0% (v/v), or at most 1.0% (v/v), preferably at most 1.0% (v/v), of the volume of the platelet-rich blood composition to which the one or more water-soluble calcium salts are added.

The term "particle" as used herein refers to a small object having a certain shape, preferably a symmetric and homogeneous shape. Non-limiting examples of particle shapes include cube, sphere, cylinder, cone, pyramid, prism, cuboid and torus; preferably sphere.

In particular embodiments, the glass particles are spheres, cubes, cylinders, cones, pyramids, prisms, cuboids, torus or combinations thereof, preferably spheres.

In particular embodiments, the glass particles have an average particle size or an average diameter from 0.20 mm to 40.0 mm, from 0.50 mm to 35.0 mm, 0.50 mm to 30.0 mm, from 0.50 mm to 25.0 mm, from 0.50 mm to 20.0 mm, from 0.50 mm to 15.0 mm, from 0.50 mm to 10.0 mm, from 1.0 mm to 10.0 mm, from 1.0 mm to 9.0 mm, from 1.0 mm to 8.0 mm, from 1.0 mm to 7.0 mm, from 1.0 mm to 6.0 mm, from 1.0 mm to 5.0 mm or from 1.0 mm to 4.0 mm, preferably from 2.0 mm to 4.0 mm. In preferred embodiments, the glass particles have an average particle size or an average diameter from 1.0 mm to 5.0 mm, preferably from 2.0 mm to 4.0 mm The particle size may be calculated based on the surface area of a given particle, also known as area-based particle size. The area-based particle size equals the diameter of the sphere that has the same surface area as a given particle. The skilled person will understand that if the particle is a sphere, the particle size equals the diameter of the particle.

In particular embodiments, the maximum diameter of the glass particles is at most 4.0 cm, at most 3.50 cm, at most 3.0 cm, at most 2.50 cm, at most 2.0 cm, at most 1.50 cm, at most 1.0 cm or at most 0.50 cm.

In particular embodiments, the glass particles have a homogeneous size distribution with a standard deviation normalized on average of an at random taken population of at least 40 beads lower than 20%, preferably lower than 10%.

The term "homogeneous size distribution" refers herein to uniform physical magnitude.

In particular embodiments, the glass particles are not porous and/or not hollow.

In particular embodiments, the glass particles are made of a silica-based glass, such as soda-lime-silica glass (also referred to herein as soda-lime glass), sodium borosilicate glass, aluminosilicate glass, lead-oxide glass or fused-silica glass.

In preferred embodiments, the glass particles are soda-lime glass particles. Present inventors observed that the coagulation time in the methods as taught herein using soda-lime glass particles could be decreased compared to the coagulation time for other types of glass.

In particular embodiments, the quantity of glass particles is from 0.010 g to 1.0 g, from 0.010 g to 0.60 g, from 0.020 g to 0.60 g, from 0.030 g to 0.60 g, from 0.040 g to 0.60 g, from 0.050 g to 0.60 g, from 0.10 g to 0.50 g, from 0.10 g to 0.450 g, from 0.10 g to 0.40 g, from 0.10 g to 0.350 g, from 0.10 g to 0.30 g, from 0.150 g to 0.30 g or from 0.20 g to 0.30 g per ml of the sample, preferably from 0.10 g to 0.40 g per ml of the sample. For example, 0.25 g of glass particles per ml of the sample.

In particular embodiments, the quantity of glass particles is from 0.10 g to 0.40 g per ml of said sample and the quantity of the one or more water-soluble calcium salts is from 2.0 µmol to 10.0 µmol or from 3.0 µmol to 8.0 µmol per ml of the sample, preferably from 3.0 µmol to 8.0 µmol per ml of the sample. For example, the quantity of glass particles is 0.250 g per ml of the sample and the quantity of the one or more water-soluble calcium salts is 5.0 µmol per ml of the sample. If the quantity of one or more water-soluble calcium salts is closer to the upper limit of the ranges as disclosed herein, the quantity of glass particles can be closer to the lower limit of the ranges as disclosed herein.

A further aspect provides a system for preparing a platelet releasate or platelet lysate comprising a first container (1) having a first containing space (1'), wherein said first containing space holds a quantity ($Q_{gp}$) of glass particles (3) and is configured to receive a quantity ($Q_{bc}$) of a platelet-rich blood composition held by a second containing space (2') of a second container (2), preferably the first containing space is configured to connect to a second containing space (2') of a second container (2) holding a quantity ($Q_{bc}$) of a platelet-rich blood composition; wherein the ratio $Q_{gp}:Q_{bc}$ is from 0.010 to 0.60 gram per ml.

In particular embodiments,
(i) the first containing space (1') further holds a quantity ($Q_{cc}$) of one or more water-soluble calcium salts (4); or
(ii) the first containing space (1') is configured to receive a quantity ($Q_{cc}$) of one or more water-soluble calcium salts (4) held by a third containing space (5') of a third container (5), preferably the first containing space (1') is configured to connect to a third containing space (5') of a third container (5) holding a quantity ($Q_{cc}$) of one or more water-soluble calcium salts (4), more preferably the first containing space (1') comprises a first opening, preferably a sealable opening, configured to connect to an opening of a third containing space (5') of a third container (5) holding a quantity ($Q_{cc}$) of one or more water-soluble calcium salts (4);
wherein in either (i) or (ii) the ratio $Q_{cc}:Q_{bc}$ is from 1.0 to 12.0 µmol per ml of said platelet-rich blood composition.

In a preferred embodiment, the first containing space (1') holds a quantity ($Q_{gp}$) of glass particles (3) and a quantity ($Q_{cc}$) of one or more water-soluble calcium salts (4), preferably the first containing space (1') holds 0.10 g to 0.40 g of glass particles per ml of platelet-rich blood composition and from 3.0 µmol to 8.0 µmol of one or more water-soluble calcium salts per ml of platelet-rich blood composition.

Connection between the first containing space (1') and the second (2') containing space and/or third containing space (5') may be obtained by any methods known in the art. For example, by conduit means (e.g. one or more tube as described elsewhere herein), by a Luer-lock connection (e.g. if the second and/or third container is a needle-less syringe), by penetrating a pierceable stopper or cover with a hollow piercing spike (e.g. if the second and/or third container is a syringe with a hollow needle), by a frangible/breakaway plug (for example as described in WO8101105 or U.S. Pat. No. 5,152,755A) or combinations thereof. Such combinations may be tubes of which the proximal end is connectable to the opening in the first containing space (1') and the distal end is connectable to the opening in the second containing space (2') and/or third containing space (5'), wherein the distal end comprises a female luer-lock component (e.g. when the second and/or third container is a needleless syringe), or alternatively, wherein the distal end is sealed by a pierceable stopper or cover (e.g. when the second and/or third container is a syringe with a hollow needle).

In particular embodiments, the system as taught herein comprises
a first container (1) comprising a first containing space (1') holding a quantity ($Q_{gp}$) of glass particles (3) and one or more water-soluble calcium salts (4) configured to receive a quantity ($Q_{bc}$) of a platelet-rich blood composition held by a second containing space (2') of a second container (2); wherein the first containing space comprises a first opening, preferably a sealable opening, configured to connect to an opening of a second containing space (2') of a second container (2); and
a first tube of which the proximal end is held by a first opening in the first containing space (1') and the distal end is configured to connect to the opening in the second containing space (2'); wherein the first tube is configured to place the first containing space (1') in fluid communication with the second containing space (2'), for example by welding;
wherein the ratio $Q_{gp}:Q_{bc}$ is from 0.010 to 0.60 gram per ml of said platelet-rich blood composition and the ratio $Q_{cc}:Q_{bc}$ is from 1.0 to 12.0 µmol per ml of said platelet-rich blood composition.

In particular embodiments, the first opening of the first containing space (1') is configured to hold the proximal end of a first tube and the opening of the third containing space (5') is configured to hold the distal end of said first tube.

In particular embodiments, the system as taught herein comprises a first tube of which the proximal end is held by the first opening in the first containing space (1') and the distal end is configured to connect to or is held by an opening in the third containing space (5'), wherein the first tube is configured to connect the first container (1) to the third container (5), preferably in a leak-free manner, and to place the first containing space (1') in fluid communication with the third containing space (5').

In particular embodiments, the system as taught herein comprises
- a first container (1) comprising a first containing space (1') holding a quantity ($Q_{gp}$) of glass particles (3) configured to receive a quantity ($Q_{bc}$) of a platelet-rich blood composition held by a second containing space (2') of a second container (2); wherein the first containing space comprises a first opening, preferably a sealable opening, configured to connect to an opening of a third containing space (5') of a third container (5);
- a third container (5) having a third containing space (5') holding a quantity ($Q_{cc}$) of one or more water-soluble calcium salts (4); and
- a first tube of which the proximal end is held by a first opening in the first containing space (1') and the distal end is held by an opening in the third containing space (5'), wherein the first tube is configured to connect the first container (1) to the third container (5), preferably in a leak-free manner, and to place the first containing space (1') in fluid communication with the third containing space (5');

wherein the ratio $Q_{gp}:Q_{bc}$ is from 0.010 to 0.60 gram per ml of said platelet-rich blood composition and the ratio $Q_{cc}:Q_{bc}$ is from 1.0 to 12.0 μmol per ml of said platelet-rich blood composition.

In particular embodiments, the fluid communication between the first containing space (1') of the first container (1) and the third containing space (5') of the third container (5) may be interrupted entirely by any means known in the art. For example, the fluid communication between the first containing space (1') and the third containing space (5') may be interrupted entirely by placing a removable clamp (e.g. a tubing clamp (e.g. 340 TCS tubing clamp of Halkay/Roberts®) or a Kocher clamp) on the first tube between the first containing space (1') and the third containing space (5'). Alternatively, the fluid communication between the first containing space (1') and the third containing space (5') may be interrupted entirely by incorporating a valve between the first containing space (1') and the third containing space (5'), preferably a frangible cannula valve, which allows to regulate the fluid communication between the first containing space (1') and the third containing space (5'). The valve can be used to open and/or close the tube, thereby allowing or preventing fluid communication between the first containing space (1') and the third containing space (5'). The valve used to reversibly interrupt the fluid communication between the first containing space (1') and the third containing space (5') may be any type of valve known in the art suitable for such means, including frangible or break-away cannula valves (for example as described in WO8101105 or U.S. Pat. No. 5,152,755A), stopcocks, pressure/relief valves and one-way valves. A frangible or break-away cannula valve is typically installed in the tube in its closed formation and once the valve is opened, the fluid communication cannot be closed anymore by said valve.

In particular embodiments, the first tube of which the proximal end is held by the first opening in the first containing space (1') and the distal end is configured to connect to or is held by an opening in the third containing space (5'), comprise means for reversibly interrupting the fluid communication between the first containing space (1') and the third containing space (5'), such as an external clamp or a valve, preferably a frangible or break-away cannula valve, as described elsewhere herein.

In particular embodiments, the first containing space comprises a second opening, preferably a sealable opening, configured to connect the first containing space to the second containing space (2') of the second container (2) holding a quantity ($Q_{bc}$) of a platelet-rich blood composition. Connection between the second opening in the first containing space (1') and the opening in the second containing space (2') may be obtained by any methods known in the art, as described elsewhere herein. For example, the second opening of the first containing space (1') may be configured to hold conduit means, such as a tube, as described elsewhere herein.

In particular embodiments, the system as taught herein comprises a second tube of which the proximal end is held by the second opening in the first containing space (1') and the distal end is configured to connect to an opening in the second containing space (2'), wherein the second tube is configured to connect the first container (1) to the second container (2), preferably in a leak-free manner, and to place the first containing space (1') in fluid communication with the second containing space (2').

In particular embodiments, the first containing space (1') is configured to release a quantity of platelet releasate held by the first containing space (1') of the first container (1) into a fourth containing space of a fourth container, wherein the fourth containing space is configured to receive (e.g. collect) and/or hold the platelet releasate prepared using the system as taught herein. Preferably the first containing space (1') is configured to connect to the fourth containing space of the fourth container.

Connection between the first containing space (1') and the fourth containing space may be obtained by any methods known in the art as described elsewhere herein.

In particular embodiments, the first containing space comprises a third opening, preferably a sealable opening, configured to connect the first containing space to a fourth containing space of a fourth container, wherein the fourth containing space is configured to receive (e.g. collect) and/or hold the platelet releasate prepared using the system as taught herein. Connection between the third opening in the first containing space (1') and the opening in the fourth containing space may be obtained by any methods known in the art, as described elsewhere herein. For example, the third opening of the first containing space (1') may be configured to hold conduit means, such as a tube, as described elsewhere herein.

In particular embodiments, the system as taught herein comprises a third tube of which the proximal end is held by the third opening in the first containing space (1') and the distal end is configured to connect to an opening in the fourth containing space of a fourth container, wherein the tube is configured to connect the first container (1) with the fourth container, preferably in a leak-free manner, and to place the first containing space (1') in fluid communication with the fourth containing space.

In particular embodiments, the first, second and/or third opening in the first containing space (1') refers to one and the same opening in the first containing space (1'). The opening in the first containing space may be connected consecutively to the second (2'), third (5') and fourth containing space.

The distal ends of the first, second and third tube of which the proximal ends are held by the first, second and third openings in the first containing space, respectively, may be connected to an opening in the third, second or fourth containing space, respectively, by connecting the distal ends of the first, second and third tube immediately to the opening in the third, second or fourth containing space, respectively, for example by a luer-lock connection or by piercing a piercable stopper which seals the opening of one containing space by a hollow needle which is in fluid connection with the other containing space, or alternatively, by interconnecting the distal end of the first, second and third tube with the distal end of a tube of which the proximal end is held by the opening in the third, second or fourth containing space, respectively, for example by a sterile tubing connection, such as by welding the tubes to each other such that the tubes are in fluid communication with each other. Sterile welding devices allow to connect or disconnect at least two tube endings while maintaining sterility during cutting and welding. In particular embodiments, if sterile welding is used to disconnect at least two tube endings, the two tubes are typically permanently sealed, and can only be reopened by cutting and/or welding.

Welding may be used to connect or disconnect tubes and allows for opening or closing the fluid communication between the containing spaces of the containers as disclosed herein without exposing the containing spaces or the content thereof to the environment (and pathogens which may be present in the environment) outside of the system as taught herein.

In particular embodiments, the first, second and third tube are flexible tubes. The tubes may be made out of any medical-grade material known in the art for preparing flexible tubings, such as plastic or silicone. In particular embodiments, the first, second and third tube consist of plastic, such as thermoplastic elastomer tubing, such as polyvinyl chloride (PVC), polyurethane (PU), fluorinated ethylene propylene (FEP), polycarbonate (PC), polyethylene (PE) such as high-density PE (HDPE) or low-density PE (LDPE), or combinations thereof, preferably PVC, PU or combinations thereof. The plastic may be sterilized by any methods or means known in the art. For example, the plastic may be treated with ethylene oxide.

In particular embodiments, the system further comprises filtering means (7) configured to retain the glass particles and/or debris within the first containing space of the first container while allowing the platelet releasate or platelet lysate as taught herein to exit the first containing space of the first container into a fourth containing space of a fourth container. The third opening of the first containing space may function as such filtering means (7) if the third opening is configured to retain the glass particles within the first containing space while allowing the platelet releasate or platelet lysate as taught herein to exit the first containing space into the fourth containing space, for example by providing a third opening having diameter which is smaller than the particle size or diameter of the smallest glass particle or providing a third opening comprising a filter (e.g. a grid) having a pore size which is smaller than the particle size or diameter of the smallest glass particle.

In particular embodiments, the filtering means (7) are in fluid communication with the first containing space of the first container and the fourth containing space of the fourth container. In particular embodiments, the filtering means (7) are located between the third opening in the first containing space of the first container and the fourth containing space of the fourth container. For example, the filtering means (7) may be present in conduit means (e.g. a tube as described elsewhere herein) between the third opening in the first containing space of the first container and the fourth containing space of the fourth container.

In particular embodiments, the filtering means (7) are one or more (e.g. one, two, three, four, five or more) filters. In particular embodiments, the filtering means (7) comprise at least one filter having a pore size which is smaller than the particle size or diameter of the smallest glass particle, such as a pore size smaller than 3.0 mm. In more particular embodiments, the filtering means (7) comprise at least one filter having a pore size which is less than 0.20 μm.

In a preferred embodiment, the system as taught herein comprises
  a first container (1) having a first containing space (1') holding a quantity ($Q_{gp}$) of glass particles (3) configured to receive a quantity ($Q_{bc}$) of a platelet-rich blood composition held by a second containing space (2') of a second container (2); wherein the first containing space comprises
    a first opening, preferably a sealable opening, configured to connect to an opening of a third containing space (5') of a third container (5);
    a second opening, preferably a sealable opening, configured to connect to an opening of the second containing space (2') of a second container (2);
    a third opening, preferably a sealable opening, configured to connect to an opening of a fourth containing space of a fourth container;
  a third container (5) having a third containing space (5') holding a quantity ($Q_{cc}$) of one or more water-soluble calcium salts (4);
  a first tube of which the proximal end is held by the first opening in the first containing space (1') and the distal end is held by an opening in the third containing space (5'), wherein the tube is configured to connect the first container (1) to the third container (5), preferably in a leak-free manner, and to place the first containing space (1') in fluid communication with the third containing space (5');
  a second tube of which the proximal end is held by the second opening in the first containing space (1') and the distal end is connectable to the second containing space (2'), wherein the second tube is configured to connect the first container (1) to the second container (2), preferably in a leak-free manner, and to place the first containing space (1') in fluid communication with the second containing space (2');
  a third tube of which the proximal end is held by the third opening in the first containing space (1') and the distal end is connectable to a fourth containing space of a fourth container, wherein the tube is configured to connect the first container (1) with the fourth container, preferably in a leak-free manner, and to place the first containing space (1') in fluid communication with the fourth containing space; and
  optionally filtering means (7) which are located between the third opening in the first containing space (1') and the fourth containing space;
  wherein the ratio $Q_{gp}:Q_{bc}$ is from 0.010 to 0.60 gram per ml of said platelet-rich blood composition and the ratio $Q_{cc}:Q_{bc}$ is from 1.0 to 12.0 μmol per ml of said platelet-rich blood composition.

In particular embodiments, the ratio $Q_{gp}:Q_{bc}$ (g/ml) is from 0.010 to 1.0, from 0.010 to 0.60, from 0.050 to 0.60, from 0.10 to 0.50, from 0.10 to 0.450, from 0.10 to 0.40, from 0.10 to 0.350, from 0.10 to 0.30, from 0.150 to 0.30 or from 0.20 to 0.30, preferably from 0.10 to 0.40. For example, 0.20 g/ml.

In particular embodiments, the ratio $Q_{cc}:Q_{bc}$ (μmol/ml) is from 0.010 to 20.0, from 0.050 to 20.0, from 0.10 to 15.0, from 0.050 to 12.0, from 1.0 to 12.0, from 0.050 to 10.0, from 0.50 to 10.0, from 1.0 to 10.0, from 1.0 to 9.0, from 1.0 to 8.0, from 1.0 to 7.0, from 1.0 to 6.0, from 2.0 to 10.0, from 2.0 to 9.0, from 0.050 to 8.0, from 2.0 to 8.0, from 3.0 to 8.0, from 2.0 to 7.0, from 3.0 to 7.0, from 2.0 to 6.0 or from 3.0 to 6.0, preferably from 1.0 to 12.0 or from 2.0 to 10.0, more preferably from 3.0 to 8.0. For example, 4.0 or 5.0 µmol/ml.

In particular embodiments, $Q_{bc}$ is from 100.0 ml to 500.0 ml, $Q_{gp}$ is from 20.0 g to 100.0 g and $Q_{cc}$ is from 2.0 µmol to 10.0 µmol.

In particular embodiments, the first containing space has a volume from 5.0 ml to 50 000.0 ml, from 10.0 ml to 10 000.0 ml, from 10.0 ml to 5 000.0 ml, from 10.0 ml to 2 500.0 ml, from 10.0 ml to 1 000.0 ml, from 50.0 ml to 750.0 ml, from 50.0 ml to 500.0 ml, from 100.0 ml to 500.0 ml, from 150.0 ml to 450.0 ml, preferably from 100.0 to 500.0 ml.

In particular embodiments, the volume of the third containing space is at most 5.0% (v/v), at most 4.0% (v/v), at most 3.0% (v/v), at most 2.0% (v/v), or at most 1.0% (v/v), preferably at most 1.0% (v/v), of the volume of the first containing space.

In particular embodiments, the third containing space has a volume from 0.10 ml to 25.0 ml, from 0.50 ml to 20.0 ml, from 1.0 ml to 15.0 ml, from 5.0 ml to 15.0 ml, from 5.0 ml to 10.0 ml, preferably from 1.0 to 15.0 ml.

The skilled person will understand that the particular embodiments with regard to the uses and the methods for preparing platelet releasate or lysate from a sample of a platelet-rich blood composition obtained from a subject as taught herein, for example with regard to the types of glass particles and water-soluble calcium salts, are also applicable to the system as taught herein.

A further aspect provides the use of the system as taught herein for producing platelet releasate or platelet lysate.

A further aspect provides a method for preparing platelet releasate from a sample of a platelet-rich blood composition obtained from a subject comprising the steps of
  a) contacting said sample with from 0.010 g to 0.60 g of glass particles per ml of said sample and from 0.10 µmol to 20.0 µmol of one or more water-soluble calcium salts per ml of said sample thereby obtaining a mixture;
  b) allowing the mixture obtained in step a) to coagulate thereby obtaining a coagulum and platelet releasate; and
  c) recovering the platelet releasate obtained in step b) from the mixture.

The term "contact" or "contacting" as used herein means bringing one or more first components (such as one or more molecules, biological entities, or materials) together with one or more second components (such as one or more molecules, biological entities, or materials) in such a manner that the first component(s) can—if capable thereof—bind or modulate the second component(s) or that the second component(s) can—if capable thereof—bind or modulate the first component(s). Such modulation may occur either directly, i.e., by way of direct interaction between the first and second component(s); or indirectly, e.g., when the first component(s) interact with or modulate one or more further component(s), one or more of which in turn interact with or modulate the second component(s), or vice versa. The term "contacting" may depending on the context be synonymous with "exposing", "incubating", "mixing", "reacting", "treating", or the like.

In particular embodiments, the sample is contacted with from 0.010 g to 1.0 g, from 0.010 g to 0.60 g, from 0.050 g to 0.60 g, from 0.10 g to 0.50 g, from 0.10 g to 0.450 g, from 0.10 g to 0.40 g, from 0.10 g to 0.350 g, from 0.10 g to 0.30 g, from 0.150 g to 0.30 g or from 0.20 g to 0.30 g glass particles per ml of the sample, preferably from 0.10 g to 0.40 g glass particles per ml of the sample.

In particular embodiments, the sample is contacted with from 0.010 µmol to 20.0 µmol, from 0.050 µmol to 20.0 µmol, from 0.10 µmol to 15.0 µmol, from 0.050 µmol to 12.0 µmol, from 1.0 µmol to 12.0 µmol, from 0.050 µmol to 10.0 µmol, from 0.50 µmol to 10.0 µmol, from 1.0 µmol to 10.0 µmol, from 1.0 µmol to 9.0 µmol, from 1.0 µmol to 8.0 µmol, from 1.0 µmol to 7.0 µmol, from 1.0 µmol to 6.0 µmol, from 2.0 µmol to 10.0 µmol, from 2.0 µmol to 9.0 µmol, from 0.050 µmol to 8.0 µmol, from 2.0 µmol to 8.0 µmol, from 3.0 µmol to 8.0 µmol, from 2.0 µmol to 7.0 µmol, from 3.0 µmol to 7.0 µmol, from 2.0 µmol to 6.0 µmol or from 3.0 µmol to 6.0 µmol of one or more water-soluble calcium salts per ml of the sample, preferably from 1.0 µmol to 12.0 µmol or from 2.0 µmol to 10.0 µmol of one or more water-soluble calcium salts per ml of the sample, more preferably from 3.0 µmol to 8.0 µmol of one or more water-soluble calcium salts per ml of the sample. For example, 4.0 µmol or 5.0 µmol of one or more water-soluble calcium salts per ml of the sample.

In particular embodiments, the sample is contacted with from 0.010 mM to 20.0 mM, from 0.050 mM to 20.0 mM, from 0.10 mM to 15.0 mM, from 0.050 mM to 12.0 mM, from 1.0 mM to 12.0 mM, from 0.050 mM to 10.0 mM, from 0.50 mM to 10.0 mM, from 1.0 mM to 10.0 mM, from 1.0 mM to 9.0 mM, from 1.0 mM to 8.0 mM, from 1.0 mM to 7.0 mM, from 1.0 mM to 6.0 mM, from 2.0 mM to 10.0 mM, from 2.0 mM to 9.0 mM, from 0.050 mM to 8.0 mM, from 2.0 mM to 8.0 mM, from 3.0 mM to 8.0 mM, from 2.0 mM to 7.0 mM, from 3.0 mM to 7.0 mM, from 2.0 mM to 6.0 mM or from 3.0 mM to 6.0 mM of one or more water-soluble calcium salts, preferably from 1.0 mM to 12.0 mM or from 2.0 mM to 10.0 mM of one or more water-soluble calcium salts, more preferably from 3.0 mM to 8.0 mM of one or more water-soluble calcium salts. For example, 4.0 mM or 5.0 mM of one or more water-soluble calcium salts.

In particular embodiments, the sample is contacted with from 0.10 g to 0.40 g of glass particles per ml of said sample and from 3.0 µmol to 8.0 µmol of one or more water-soluble calcium salts per ml of said sample. For example, the sample is contacted with about 0.100 to 0.300 g glass particles per ml of sample, such as about 0.150 to 0.250 g glass particles per ml of sample, for example about 0.200 g glass particles per ml of the sample and between 4.0 and 6.0 µmol, such as about 5.0 µmol of one or more water-soluble calcium salts per ml of the sample.

In particular embodiments, step a) (i.e. contacting the sample with glass particles and calcium salts) of the methods as taught herein comprises mixing the sample, the glass particles and the one or more water-soluble calcium salts using a mixing means, such as a rotator, agitator or shaker (e.g. a rocking shaker).

The term "coagulate" or "clot" as used herein refers to the sequential process by which a fully retracted coagulum or clot is formed from whole blood or a whole blood-derivative. Coagulation can be initiated by the activation of the intrinsic or extrinsic coagulation pathway. Both pathways result in the production of coagulation factor Xa. The activation of coagulation factor Xa will initiate the common pathway of coagulation, which ultimately results in the formation of a coagulum or clot. The extrinsic pathway is typically initiated by the response to tissue factor (TF), which may occur when there is an open connection between the outer and inner surface of a blood vessel (e.g. a broken blood vessel). TF activates Factor VII, forming Factor VIIa, which triggers a cascade of reactions that result in the rapid production of Factor Xa. On the other hand, the intrinsic pathway is activated by injury that occurs within the blood vessel. This pathway is initiated by the activation of factor XII. Factor XII activation to Factor XIIa may occur at any time when blood comes into contact with a surface of negative charge, for instance when in contact with non-biological matrices. A cross-activation may occur between the intrinsic pathway and the extrinsic pathway. For example, in addition to activating Factor Xa, Factor VIIa activates Factor IX, a necessary component of the intrinsic pathway. The production of Factor Xa results in the cleavage of prothrombin (Factor II) to thrombin (Factor IIa). Next, thrombin catalyzes the conversion of fibrinogen (Factor I) into long, sticky threads of insoluble fibrin. The fibrin threads form a mesh that traps platelets, plasma and optionally blood cells. The fibrin meshwork subsequently contracts and squeezes out at least 95% of its original fluid content, also known as clot retraction, thereby obtaining the coagulum or clot and the expelled fluid.

By using glass particles in combination with one or more water-soluble calcium salts as taught herein a stable coagulum will be formed entrapping the glass particles as well as platelet remnants. The platelet releasate or platelet lysate obtained by the methods, uses or methods as taught herein will require less or no filtration before use as the platelets are trapped in the coagulum which is stabilized by the glass particles.

In particular embodiments, the glass particles and the one or more water-soluble calcium salts are the only coagulation activators used in the uses or methods as taught herein (i.e. in the addition of the potential coagulation activators already present in the platelet-rich blood composition, such as FXII). Importantly, in embodiments no additional blood coagulation activators are added.

The term "coagulation activator" as used herein refers to substances which can initiate coagulation by the intrinsic and/or extrinsic coagulation pathway. Non-limiting examples of coagulation activators include thrombins, such as e.g. exogenous human purified or recombinant thrombin or (lyophilized) bovine thrombin, tissue factors, such as e.g. exogenous rabbit tissue factor or purified or recombinant human tissue factor, synthetic phospholipids in combination with aminophospholipids, Russel's viper venom, ecarin, textarin, elagic acid, kaolin and other clay minerals.

In particular embodiments, the uses or methods as taught herein do not comprise the use of one or more coagulation activators as defined herein.

In particular embodiments, in step b) (i.e. allowing the mixture to coagulate) of the methods as taught herein said mixture is allowed to coagulate for a period from 1 hour to 20 hours, from 1 to 18 hours, from 1 to 16 hours, from 1 to 14 hours, from 1 to 12 hours, from 1 to 10 hours, from 1 to 8 hours, from 1 to 6 hours, from 1 to 4 hours, preferably from 2 to 6 hours, more preferably from 2 to 4 hours. For example, said mixture is allowed to coagulate for a period of 3 hours.

In particular embodiments, step b) of the methods as taught herein is performed at a temperature from 5° C. to 42° C., from 15° C. to 40° C., from 20° C. to 40° C., from 15° C. to 25° C., from 20 to 25° C., preferably from 15° C. to 40° C. For example, step b) of the methods as taught herein is performed at room temperature or at about 37° C. After having contacted the platelet-rich blood composition with glass particles and the one or more water-soluble calcium salts and allowing the mixture obtained in step a) to coagulate thereby obtaining a coagulum and platelet releasate, the glass particles (e.g. encompassed by the coagulum) are preferably removed from all or part of the platelet releasate so as to prevent interference of the glass particles in the further use of the platelet releasate. Accordingly, in particular embodiments, at least part, preferably substantially all (e.g. at least 70%, at least 75%, at least 80%, at least 85%, at least 90% or at least 95%, preferably at least 95%), of the platelet releasate is recovered from the sample, i.e. removed from physical contact with the glass particles (e.g. encompassed by the coagulum).

In particular embodiments, said in step c) said platelet releasate obtained in step b) is recovered from the mixture by simply collecting the liquid phase containing the releasate or by centrifugation.

In particular embodiments, said in step c) said platelet releasate obtained in step b) is recovered from the mixture by passing the mixture through at least one filter.

The term "filter" as used herein has its ordinary meaning in that it refers to a porous substance, device or membrane through which liquid is passed to remove suspended impurities or solid particles and/or to recover solids.

In particular embodiments, the filter is a membrane filter, such as a microporous nitrocellulose, polyurethane and/or polyester film.

The term "pore size" refers to the mean size of the one or more pores on a membrane surface or filter. The pore size also relates to the filter's ability to filter out particles of a certain size. For example, a filter with a pore size of 0.50 μm will filter out particles with a diameter of 0.50 μm or more from a filtration stream. Pore size may be determined by any methods known by the skilled person to determine pore size such as visual examination using scanning electron microscopy, porosimetry, correlation spectroscopy and/or single particle tracking. Pores may be cylindrical or sponge pores.

In particular embodiments, the filter has at least one (e.g. one, two, three, four, five or more) pore.

In particular embodiments, said in step c) said platelet releasate obtained in step b) is recovered from the mixture by passing the mixture through at least one (e.g. one, two, three, four, five or more) filter, wherein the at least one filter has a pore size which is smaller than the particle size or diameter of the smallest glass particle. The filter may be any filter known in the art for filtering paleIet releaste or platelet lysate, such as the MZP of the MZP Series Capsules (ZenPure, Hitma), Sartopure® GF Plus filters (Sartorius stedim biotech) and Sartopure® PP3 filters (Sartorius stedim biotech).

In particular embodiments, said in step c) said platelet releasate obtained in step b) is recovered from the mixture by passing the mixture through at least one filter (e.g. one, two, three, four, five or more), wherein at least one filter has a pore size which is smaller than the particle size or diameter of the smallest glass particle and less than 0.2 μm.

In particular embodiments, the passing of the platelet releasate through the filter may be achieved by any methods known by the skilled person. For example, the passing of the platelet releasate through the filter may be achieved by gravity, vacuum, or pressure.

In particular embodiments, the methods for preparing a platelet releasate as taught herein do not comprise a step of lysing the platelets present in the platelet-rich blood composition.

In particular embodiments, the methods as taught herein optionally comprise lysing the platelets present in the platelet-rich blood composition obtaining a platelet lysate. If such a lysing step is present, the method as taught herein will be a method for preparing a platelet lysate and a platelet lysate will be obtained from such obtained coagulum and/or platelet releasate.

In particular embodiments, the methods as taught herein optionally comprise lysing the platelets present in the obtained coagulum and/or platelet releasate obtained in step b) thereby obtaining a platelet lysate. Platelet lysis may be obtained by any methods known in the art for lysing platelets including freeze-thaw cycles, sonication, chemical lysis (e.g. using Triton X-100), mechanical disruption and liquid or high pressure homogenization.

In particular embodiments, the methods as taught herein further comprises at least one (e.g. one, two, three, four, five or more) steps of freezing and thawing the coagulum and/or platelet releasate obtained in step b) thereby obtaining a platelet lysate. Freezing and thawing of the coagulum and/or platelet releasate obtained in step b) may be performed by any method known in the art for freezing and thawing platelet-rich blood compositions in order to destruct the platelets. For example, as described in Fekete et al, Platelet lysate from whole blood-derived pooled platelet concentrates and apheresis-derived platelet concentrates for the isolation and expansion of human bone marrow mesenchymal stromal cells: production process, content and identification of active components. Cytotherapy 2012; 14(5):540-54). The skilled person will understand that increasing the number of freeze-thaw cycles above three may not further increase the concentration of growth factors in the platelet lysate (Strandberg et al., Standardizing the freeze-thaw preparation of growth factors from platelet lysate. Transfusion, 2017; 57(4):1058-65). Furthermore, freeze-thaw cycles are often time-consuming and may damage the container containing the platelet lysate. In view thereof, the methods as taught herein preferably comprises at most three, at most two, or at most one, preferably at most one, step(s) of freezing and thawing.

In particular embodiments, the mixture obtained in step a) is frozen at −20° C. or less, at −25° C. or less, at −30° C. or less, at −35° C. or less, at −40° C. or less, at −45° C. or less, at −50° C. or less, at −55° C. or less, at −60° C. or less, at −65° C. or less, at −70° C. or less, at −75° C. or less, at −80° C. or less, at −100° C. or less, at −150° C. or less, at −200° C. or less, preferably at −80° C. or less. For example, the mixture obtained in step a) is frozen at a temperature of −80° C. or at a temperature from −196° C. to −210° C. (e.g. in liquid nitrogen).

In particular embodiments, the mixture obtained in step a) is frozen for at least 0.5 hours, at least 1 hour, at least 2 hours, at least 4 hours, at least 6 hours, at least 8 hours, at least 10 hours, at least 12 hours, at least 14 hours, at least 16 hours, at least 18 hours, at least 20 hours, at least 22 hours, at least 24 hours, at least 26 hours, at least 28 hours or at least 30 hours, preferably at least 24 hours. For example, the mixture obtained in step a) is frozen for 24 hours.

In particular embodiments, the mixture obtained in step a) is thawed after freezing at a temperature of at least 3° C., at least 4° C., at least 5° C., at least 10° C., at least 15° C., at least 20° C., at least 25° C., at least 30° C., at least 35°, at least 36° C. or at least 37° C. For example, the mixture obtained in step a) may be thawed at 4° C. (such as in a fridge), at room temperature, or at 37° C. (such as in a warm water bath).

In particular embodiments, the at least one step (such as one, two, three or more) of freezing and thawing is performed prior to step c).

In particular embodiments, the methods for preparing platelet releasate as taught herein comprise a step of storing the platelet releasate recovered in step c).

In particular embodiments, the methods for preparing platelet releasate as taught herein comprises a step of lyophilizing the platelet releasate or platelet lysate.

In particular embodiments, the methods for preparing platelet releasate or lysate as taught herein does not comprise a step of actively adding polypeptides, proteins, peptides, lipids, carbohydrates or nucleic acids of non-human mammals to the platelet-rich composition, the glass particles, the one or more water-soluble calcium salts, the platelet releasate and/or the platelet lysate. For example, the methods for preparing platelet releasate or lysate as taught herein does not comprise a step of actively adding heparin derived from a non-human mammal, such as bovine or porcine heparin, to the platelet-rich composition, the glass particles, the one or more water-soluble calcium salts, the platelet releasate and/or the platelet lysate.

Currently existing methods for preparing platelet releasate or lysate are currently not performed in a closed system which increases the risk of contamination of the platelet releasate or lysate with ambient pathogens.

In particular embodiments, the method for preparing platelet releasate or platelet lysate as taught herein is performed under sterile conditions and is performed in an essentially closed system. As a result hereof, the platelet releasate or platelet lysate obtained by the method as taught herein are substantially free from ambient pathogens (i.e. pathogens which were not yet present in the platelet-rich blood composition before initiating the method as taught herein).

In particular embodiments, the methods for preparing platelet releasate as taught herein are performed using the system for preparing platelet releasate as taught herein.

In a preferred embodiment, the methods for preparing platelet releasate as taught herein comprise the following steps:
  placing a first containing space (1') of a first container (1) and a second containing space (2') of a second container (2) in fluid communication; wherein said first containing space (1') (i) is configured to receive a quantity ($Q_{bc}$) of a platelet-rich blood composition held by a second containing space (2') of a second container (2); and (ii) holds a quantity ($Q_{gp}$) of glass particles (3) and a quantity ($Q_{gg}$) of one or more water-soluble calcium salts (4); and wherein said second containing space (2') holds a quantity ($Q_{bc}$) of a platelet-rich blood composition;
  allowing the platelet-rich blood composition to flow from the second containing space (2') into to the first containing space (1');
  optionally disrupting the fluid communication between the second containing space (2') and the first containing space (1');
  mixing the platelet-rich blood composition, the glass particles (3) and the one or more water-soluble calcium salts (4) thereby obtaining a mixture;
  allowing the obtained mixture to coagulate thereby obtaining a coagulum and platelet releasate;
  placing the first containing space (1') of the first container (1) and a fourth containing space of a fourth container in fluid communication, wherein the fourth containing space is configured to receive and/or hold the platelet releasate prepared using the system;
  recovering the platelet releasate obtained in step b) from the mixture; and optionally disrupting the fluid communication between the fourth containing space and the first containing space (1').

In particular embodiments, the methods for preparing platelet releasate as taught herein comprise the following steps:
- placing a first containing space (1') of a first container (1) in fluid communication with a second containing space (2') of a second container (2); wherein said second containing space (2') hold a quantity ($Q_{bc}$) of a platelet-rich blood composition; wherein said first containing space (1') (i) is configured to receive a quantity ($Q_{bc}$) of a platelet-rich blood composition comprised in a second containing space (2') of a second container (2); (ii) holds a quantity ($Q_{gp}$) of glass particles (3); and (iii) comprises a first opening configured to connect to an opening of a third containing space (5') of a third container (5), and wherein said third containing space (5') comprises a quantity ($Q_{gg}$) of one or more water-soluble calcium salts (4);
- allowing the platelet-rich blood composition to flow from the second containing space (2') into to the first containing space (1');
- optionally disrupting the fluid communication between the first containing space (1') and the second containing space (2');
- placing the third containing space (5') of the third container (5) holding a quantity ($Q_{gg}$) of one or more water-soluble calcium salts (4) in fluid communication with the first containing space (1'), allowing the one or more water-soluble calcium salts (4) to flow from the third containing space (5') into the first containing space (1'); and optionally disrupting the fluid communication between the third containing space (5') and the first containing space (1');
- mixing the platelet-rich blood composition, the glass particles and the one or more water-soluble calcium salts thereby obtaining a mixture;
- allowing the obtained mixture to coagulate thereby obtaining a coagulum and platelet releasate;
- placing the first containing space (1') of the first container (1) and a fourth containing space of a fourth container in fluid communication;
- recovering (6) the platelet releasate obtained in step b) from the mixture; and
- optionally disrupting the fluid communication between the fourth containing space and the first containing space (1').

In particular embodiments, placing the second containing space (2') of a second container (2) in fluid communication with the first containing space (1') of a first container (1) placing the third containing space (5') of the third container (5) in fluid communication with the first containing space (1') of a first container (1); and/or placing the fourth containing space of the fourth container in fluid communication with the first containing space (1') of a first container (1) are performed by a sterile tubing connection as known in the art.

This way, the methods and systems as disclosed herein provide a completely sterile and closed system for preparing a platelet releasate or platelet lysate.

In particular embodiments, if for example the third container is a syringe comprising a hollow needle, placing the third containing space (5') of the third container (5) in fluid communication with the first containing space (1') may be performed by injecting the quantity ($Q_{cc}$) of one or more water-soluble calcium salts (4) into the first containing.

In particular embodiments, placing the second containing space (2') of the second container (2) in fluid communication with the first containing space (1') of the first container (1) and/or disrupting the fluid communication between the first containing space (1') and the second containing space (2'); maybe performed by welding. For example, for placing the second containing space (2') of a second container (2) in fluid communication with the first containing space (1') of a first container (1) a tube which is in fluid communication with the first containing space (1') may be welded to a tube which is in fluid communication with the second containing space (2') as known in the art.

Similarly, in particular embodiments, placing the third containing space (3') of the third container (3) in fluid communication with the first containing space (1') of the first container (1) may be performed by welding. For example, for placing the third containing space (3') of the third container (3) in fluid communication with the first containing space (1') of the first container (1) a tube which is in fluid communication with the third containing space (3') may be welded to a tube which is in fluid communication with the first containing space (1').

In particular embodiments, placing the fourth containing space of the fourth container in fluid communication with the first containing space (1') of the first container (1) and/or disrupting the fluid communication between the first containing space (1') and the fourth containing space; may be performed by welding. For example, for placing the fourth containing space of the fourth container in fluid communication with the first containing space (1') of the first container (1) a tube which is in fluid communication with the first containing space (1') may be welded to a tube which is in fluid communication with the fourth containing space (2') as known in the art.

In particular embodiments, the welding is performed using a sterile tube welder. For example, a TSCD® II or TSCD-Q® sterile tubing welder from Terumo. The skilled person will understand that the particular embodiments with regard to the uses and the systems for preparing platelet releasate as taught herein are also applicable to the method for preparing platelet releasate from a sample of a platelet-rich blood composition as taught herein and vice versa. A further aspect provides a platelet releasate obtained by the methods as taught herein.

In particular embodiments, the platelet releasate obtained by the methods as taught herein comprises coagulation factors, small molecules, energy equivalents, chemokines, cytokines, adhesion molecules, hormones, immunologic molecules and regulators of growth (or growth factors), cell division, apoptosis and/or angiogenesis and/or attachment factors.

The term "attachment factors" as used herein refers to structural proteins or protein-like substances that have adherent capabilities and increase cell-substrate interactions between anchorage-dependent cells and a substrate such as a cell culture flask. Non-limiting examples of attachment factors include fibronectin, vitronectin, Von willebrand factor, glycocalicin and sCD62P.

In particular embodiments, the platelet releasate obtained by the methods as taught herein comprises one or more growth factors selected from the group consisting of vascular endothelial growth factor (VEGF), fibroblast growth factor (FGF), platelet derived growth factor (PDGF), transforming growth factor-beta (TGF-beta), insulin like growth factor (IGF), epidermal growth factor (EGF), platelet factor 4 and angiopoietins. The presence or absence of these growth factors in the platelet releasate may be determined by any method known in the art, such as immunoassays (e.g. enzyme-linked immunosorbent assay (ELISA), Western blot) and proteomic assays.

In particular embodiments, the platelet releasate obtained by the methods as taught herein comprises one or more hormones selected from the group consisting of serotonine, adrenaline, histamine, thromboxanes, prostaglandines, ceramides and sphingolipids.

A further aspect provides a platelet lysate obtained by the methods as taught herein.

In particular embodiments, the platelet releasate or platelet lysate obtained by the methods as taught herein has a transmittance which is at least 45%, at least 50%, at least 55%, at least 60%, at least 65%, at least 70%, at least 75%, at least 80%, at least 85%, at least 90%, or at least 95% of the transmittance of distilled water, preferably when measured at a wavelength of 680 nm.

In particular embodiments, the platelet releasate or platelet lysate obtained by the methods as taught herein has a transmittance which is at least 80%, at least 85%, at least 90%, or at least 95%, preferably at least 90%, of the transmittance of distilled water, preferably when measured at a wavelength of 680 nm, wherein the methods as taught herein comprises at least one step of passing the platelet releasate or platelet lysate through a filter with a pore size of at most 0.2 μm.

In particular embodiments, the platelet releasate or platelet lysate as taught herein comprises a residual $Ca^{2+}$ concentration after coagulation of at most 1.5 mM, at most 1.4 mM, at most 1.3 mM, at most 1.2 mM, at most 1.1 mM, at most 1 mM, at most 0.9 mM, at most 0.8 mM, at most 0.7 mM, at most 0.6 mM, at most 0.5 mM, at most 0.4 mM, at most 0.35 mM, at most 0.34 mM, at most 0.33 mM, at most 0.32 mM, at most 0.31 mM, at most 0.3 mM, at most 0.29 mM, at most 0.28 mM, at most 0.27 mM, at most 0.26 mM or at most 0.25 mM, preferably at most 0.35 mM. The concentration of $Ca^{2+}$ (i.e. calcium ions) in the platelet releasate or platelet lysate may be determined by any methods known in the art for determining $Ca^{2+}$ ions, such as by blood gas analysis using built-in ion selective electrodes.

In particular embodiments, for example if the platelet releasate or platelet lysate is obtained from a human platelet-rich blood composition, the platelet releasate or platelet lysate as taught herein is substantially free of any polypeptides, proteins, peptides, lipids, carbohydrates (such as polysaccharides) or nucleic acids derived from a non-human mammal. The term "substantially free" when used herein in reference to polypeptides, proteins, peptides, lipids, carbohydrates (such as polysaccharides) or nucleic acids derived from a non-human mammal refers to the platelet releasate or platelet lysate as taught herein to which no polypeptides, proteins, peptides, lipids, carbohydrates or nucleic acids of non-human mammals were actively added (i.e. not inherently present therein). For example, the platelet releasate or platelet lysate as taught herein is substantially free of heparin derived from a non-human mammal, such as bovine or porcine heparin.

In particular embodiments, the platelet releasate or platelet lysate as taught herein may be comprised in a pharmaceutical or cosmetic composition.

In particular embodiments, the platelet releasate or platelet lysate as taught herein is liquid, semi-solid or solid. A solid form of the platelet releasate or platelet lysate as taught herein may be obtained by lyophilizing the platelet releasate or platelet lysate.

A further aspect provides a pharmaceutical composition comprising the platelet releasate or platelet lysate as taught herein and optionally one or more pharmaceutically acceptable carriers.

A further aspect provides a cosmetic composition comprising the platelet releasate or platelet lysate as taught herein and optionally one or more cosmetically acceptable carriers.

A further aspect provides a composition comprising a platelet-rich blood composition, from 0.10 mM to 20.0 mM of $Ca^{2+}$ ions in addition to the $Ca^{2+}$ ions present in the platelet-rich blood composition and from 0.010 g to 0.60 g of glass particles per ml of said platelet-rich blood composition.

In particular embodiments, the compositions as taught herein comprise hormones, growth factors and/or attachment factors. These hormones, growth factors and/or attachment factors are typically released from the platelets present in the platelet-rich blood composition.

In particular embodiments, the compositions as taught herein comprise one or more growth factors selected from the group consisting of vascular endothelial growth factor (VEGF), fibroblast growth factor (FGF), platelet derived growth factor (PDGF), transforming growth factor-beta (TGF-beta), insulin like growth factor (IGF) epidermal growth factor (EGF)), platelet factor 4 and angiopoietins. The presence or absence of these growth factors in the composition may be determined by any method known in the art, such as immunoassays (e.g. enzyme-linked immunosorbent assay (ELISA), Western blot) and proteomic assays In particular embodiments, said composition is comprised in a container, preferably a medical-grade container. Non-limiting examples of suitable containers include medical-grade transfer bags, flasks or bottles.

Accordingly, also provided herein is a container comprising the composition as taught herein.

In particular embodiments, said composition or container comprising the composition is stored at a temperature from −210° C. to 25° C. For example, the composition or the container may be stored at a temperature from −196° C. to −210° C. (e.g. in liquid nitrogen), at a temperature of −80° C. (e.g. in a freezer), at a temperature of −20° C. (e.g. in a freezer), at a temperature of 4° C. (e.g. in a fridge), or at room temperature. If the composition or container is stored at room temperature, the composition is preferably lyophilized before storage. The composition may be stored for a period up to one year or more (such as 2 years).

A further aspect provides the platelet releasate, the platelet lysate or the pharmaceutical composition comprising the platelet releasate or the platelet lysate as taught herein for use as a medicament.

The platelet releasate, the platelet lysate or the pharmaceutical composition comprising the platelet releasate or the platelet lysate as taught herein may be used to treat diseases or disorders in a number of medical feels of sub-speciality, including rheumatology, orthopedics, dermatology, dentistry, stomatology, optalmology, gynaecology, endocrinology and plastic surgery. Non-limiting examples of such diseases or disorders include wounds (e.g. chronic or acute wounds), hard-tissue (e.g. bone) and soft-tissue injuries, inflammatory diseases, bone diseases, osteonecrosis, ocular surface diseases, neurodegenerative disorders, peripheral arterial disease, osteoarthritis, intervertebral disc degeneration, rotator cuff injury, hamstring injury, greater trochanteric pain syndrome, arthroplasty, carpal tunnel syndrome, epicondylitis, plantar fasciitis, tendinopathies, vitiligo, alopecia, melisma, venous leg ulcer, burns, (acne) scars, dental implantation, alveolar cleft, endodontic procedures, maxillofacial surgery, glaucoma complications, neurotrophic corneal ulcer, severe dry eye syndrome, lichen sclerosis, endometrial disease, vaginal atrophy, diabetic ulcers and postoperative infections, swelling and pain.

A further aspect provides the platelet releasate, the platelet lysate or the pharmaceutical composition comprising the platelet releasate or the platelet lysate as taught herein for use in the treatment of hard- and soft-tissue injuries, inflammatory diseases (e.g. tendinitis, periodontitis, plantar fasciitis, trochanteric bursitis and epicondylatis), bone diseases (e.g. osteonecrosis), degenerative joint diseases (e.g. osteoarthritis), degenerative disc diseases (e.g. intervertebral disc degeneration), skin conditions (e.g. lichen sclerosis, skin pigmentation disorders such as vitiligo and melasma), alopecia areata, endometrial disease, vaginal atrophy, ocular surface diseases (e.g. severe dry eye syndrome, glaucoma complications such as dry eyes), carpal tunnel syndrome, neurodegenerative disorders (e.g. Parkinson's disease and Alzheimer's disease), peripheral arterial disease and pain (e.g. postoperative pain, radicular pain and low back pain (LBP), knee pain, ankle pain, hip pain and shoulder pain) comprising administering to a subject an effective amount of the platelet releasate, the platelet lysate or the pharmaceutical composition comprising the platelet releasate or the platelet lysate.

A further aspect provides a method for treating hard- and soft-tissue injuries, inflammatory diseases (e.g. tendinitis, periodontitis, plantar fasciitis, trochanteric bursitis and epicondylatis), bone diseases (e.g. osteonecrosis), degenerative joint diseases (e.g. osteoarthritis), degenerative disc diseases (e.g. intervertebral disc degeneration), skin conditions (e.g. lichen sclerosis, skin pigmentation disorders such as vitiligo and melasma), alopecia areata, endometrial disease, vaginal atrophy, ocular surface diseases (e.g. severe dry eye syndrome, glaucoma complications such as dry eyes), carpal tunnel syndrome, neurodegenerative disorders (e.g. Parkinson's disease and Alzheimer's disease), peripheral arterial disease and pain (e.g. postoperative pain, radicular pain and low back pain (LBP), knee pain, ankle pain, hip pain and shoulder pain) comprising administering an effective amount of the platelet releasate, the platelet lysate or the pharmaceutical composition comprising the platelet releasate or platelet lysate as taught herein to a subject.

The terms "treat" or "treatment" encompass both the therapeutic treatment of an already developed disease or condition, such as the therapy of already developed hard- and soft-tissue injuries, inflammatory diseases, bone diseases, degenerative joint diseases, degenerative disc diseases, skin conditions, alopecia areata, endometrial disease, vaginal atrophy, ocular surface diseases, carpal tunnel syndrome, neurodegenerative disorders, peripheral arterial disease and pain, as well as prophylactic or preventive measures, wherein the aim is to prevent or lessen the chances of incidence of an undesired affliction, such as to prevent occurrence, development and progression of hard- and soft-tissue injuries, inflammatory diseases, bone diseases, degenerative joint diseases, degenerative disc diseases, skin conditions, alopecia areata, endometrial disease, vaginal atrophy, ocular surface diseases, carpal tunnel syndrome, neurodegenerative disorders, peripheral arterial disease and pain. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "effective amount" as used herein with regard to the therapeutic use of the platelet releasate or lysate as taught herein, refers to an amount of platelet releasate or platelet lysate as taught herein or a pharmaceutical composition comprising the platelet releasate or platelet lysate as taught herein that elicits the biological or medicinal response in a subject ("therapeutically effective amount") and/or that inhibits or delays in a subject the onset of a disorder ("prophylactically effective amount") that is being sought by a surgeon, researcher, veterinarian, medical doctor or other clinician, which may include inter alia alleviation of the symptoms of the disease or condition being treated. Methods are known in the art for determining therapeutically and/or prophylactically effective doses of a platelet releasate or platelet lysate as taught herein or a pharmaceutical composition comprising the platelet releasate or platelet lysate as taught herein.

Non-limiting examples of hard- and soft-tissue injuries include ulcers (e.g. neurotrophic corneal ulcers, diabetic foot ulcers, venous leg ulcers, pressure ulcers and anal fissures), surgical wounds, burns and scars. As the platelet releasate, the platelet lysate or the pharmaceutical composition comprising the platelet releasate or the platelet lysate as taught herein can be used for the healing of hard tissues such as bone as well as soft tissues such as skin, the platelet releasate, the platelet lysate or the pharmaceutical composition comprising the platelet releasate or the platelet lysate as taught herein may be used for healing tissue injuries resulting from rotator cuff injury, hamstring injury, dental implantation, alveolar cleft repair, endodontic procedures, maxillofacial surgery, arthroplasty, blepharoplasty and facial lipofilling. A further aspect provides the use of the platelet releasate, the platelet lysate or the cosmetic composition comprising the platelet releasate or the platelet lysate as taught herein for improving the appearance of the skin and/or hair.

In particular embodiments, the use of the platelet releasate, the platelet lysate or the cosmetic composition comprising the platelet releasate or the platelet lysate as taught herein for rejuvenating the skin, improving the appearance of the skin and/or hair comprises reducing wrinkles (e.g. wrinkles in the face) and scars, increasing the firmness and elasticity of the skin, improving the texture, skin tone and/or color of the skin and/or increasing hair growth, the number of hairs, hair thickness and/or the growth phase of the hair cycle.

In particular embodiments, the use of the platelet releasate, the platelet lysate or the cosmetic composition comprising the platelet releasate or the platelet lysate as taught herein for improving the appearance of the skin and/or hair comprises topically applying a volume of the platelet releasate, the platelet lysate or the cosmetic composition comprising the platelet releasate or the platelet lysate as taught herein on the skin or injecting a volume of the platelet releasate or platelet lysate as taught herein in the epidermis, dermis or hypodermis of the skin, preferably by microneedling.

In particular embodiments, the use of the platelet releasate, the platelet lysate or the cosmetic composition comprising the platelet releasate or the platelet lysate as taught herein for improving the appearance of the skin and/or hair is not a method of treatment.

Present inventors found that the method as taught herein allows to prepare platelet releasate or platelet lysate which does not lead to the formation of precipitations when being added to growth medium.

Accordingly, a further aspect provides the use of the platelet releasate or platelet lysate as taught herein in in vitro cell culture or tissue culture.

A further aspect provides the use of the platelet releasate or platelet lysate as taught herein for maintaining cells or tissue in vitro and/or for improving growth of cells in vitro.

In particular embodiments, the use of the platelet releasate or platelet lysate as taught herein in growth medium of cells may improve the growth of cells from about 2-fold to about 5-fold—when compared to the growth of cells if the growth medium of the cells is supplemented with the same amount of serum, more particularly FBS.

A further aspect provides the use of the platelet releasate or platelet lysate as taught herein as a replacer for serum, such as FBS, in growth medium. In particular embodiments, the use of the platelet releasates or platelet lysates as taught herein in in vitro cell culture or tissue culture or for maintaining cells or tissue in vitro and/or for improving the growth of cells in vitro comprises adding an effective amount of platelet releasate or platelet lysate as taught herein to the growth medium of the cells.

Similarly, a further aspect provides an in vitro method for maintaining cells or tissue in vitro or for improving the in vitro growth of cells comprising adding an effective amount of platelet releasate or platelet lysate as taught herein to the growth medium of the cells.

The term "effective amount" as used herein with regard to the in vitro use of the platelet releasate or lysate as taught herein, refers to an amount of platelet releasate or platelet lysate as taught herein that elicits the desired in vitro biological response. Methods are known in the art for determining effective doses of platelet releasate or platelet lysate as taught herein in in vitro cell and/or tissue culture.

The term "growth medium" or "culture medium" as used herein refers to a solid, liquid or semi-solid designed to support the growth of cells or tissue. Growth medium typically comprises macronutrients (e.g. nitrogen, phosphorus, potassium, calcium, magnesium or sulfur), micronutrients (e.g. iron, manganese, zinc, boron, copper, molybdenum), vitamins, amino acids, one or more sugars (e.g. glucose), inorganic salts and/or proteins (e.g. transferrin). Growth media are well known in the art and may vary dependent on the type of cell or tissue cultured, as well as on the purpose of the culture (e.g. differentiation, expansion or maintenance). Non-limiting examples of growth media include Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, Medium 199, Waymouth's MB 752/1 or Williams Medium E, Mesenchymal Stem Cell Basal Medium and modifications and/or combinations thereof.

In particular embodiments, the growth medium comprises $CaCl_2$, $MgSO_4$, KCl, $NaHCO_3$, NaCl and phosphate or salts thereof.

In particular embodiments, the growth medium is DMEM, such as low-glucose and low-sodium pyruvate DMEM. In particular embodiments, the growth medium is DMEM and comprises about 0.2 g/L $CaCl_2$, about 0.1 g/L $MgSO_4$, about 0.4 g/L KCl, about 3.7 g/L $NaHCO_3$, about 6.4 g/L NaCl and about 0.1 g/L $Na_2HPO_4$.

In particular embodiments, the effective amount of platelet releasate or platelet lysate in the use of the platelet releasates or platelet lysates as taught herein in in vitro cell culture or tissue culture or for improving in vitro cell growth comprises adding an effective amount of platelet releasate or platelet lysate as taught herein and the methods for improving cell growth as taught herein is at least 0.5% (v/v), at least 1.0% (v/v), at least 2.0% (v/v), at least 3.0% (v/v), at least 4.0% (v/v), at least 5.0% (v/v), at least 6.0% (v/v), at least 7.0% (v/v), at least 8.0% (v/v), at least 9.0% (v/v), at least 10.0% (v/v), at least 11.0% (v/v), at least 12.0% (v/v), at least 13.0% (v/v), at least 14.0% (v/v) of at least 15.0% (v/v), of at least 20.0% (v/v), preferably between 5 to 15% (v/v/), or between 8 to 12% (v/v), such as about 10.0% (v/v) of the growth medium.

In particular embodiments, the cells are pluripotent stem cells (PS), such as mammalian PS and human PS, preferably human PS. In more particular embodiments, the cells are induced PS.

The term "stem cell" refers generally to an unspecialized or relatively less specialized and proliferation-competent cell, which is capable of self-renewal, i.e., can proliferate without differentiation, and which or the progeny of which can give rise to at least one relatively more specialized cell type. The term encompasses stem cells capable of substantially unlimited self-renewal, i.e., wherein the progeny of a stem cell or at least part thereof substantially retains the unspecialized or relatively less specialized phenotype, the differentiation potential, and the proliferation capacity of the mother stem cell, as well as stem cells which display limited self-renewal, i.e., wherein the capacity of the progeny or part thereof for further proliferation and/or differentiation is demonstrably reduced compared to the mother cell. By means of example and not limitation, a stem cell may give rise to descendants that can differentiate along one or more lineages to produce increasingly relatively more specialized cells, wherein such descendants and/or increasingly relatively more specialized cells may themselves be stem cells as defined herein, or even to produce terminally differentiated cells, i.e., fully specialized cells, which may be post-mitotic.

As used herein, the qualifier "pluripotent" denotes the capacity of a cell to give rise to cell types originating from all three germ layers of an organism, i.e., mesoderm, endoderm, and ectoderm, and potentially capable of giving rise to any and all cell types of an organism, although not able of growing into the whole organism.

In particular embodiments, the cells are pluripotent stem cells (PS) selected from the group consisting of mesenchymal stem cells (MSCs), blood-derived stem cells (BDSCs), umbilical cord-blood derived stem cells (UCBSCs) and bone marrow-derived stem cells (BMSCs). In preferred embodiments, the cells are MSCs.

The term "mesenchymal stem cell" or "MSC" as used herein refers to an adult, mesoderm-derived stem cell that is capable of generating cells of mesenchymal lineages, typically of two or more mesenchymal lineages, more typically three or more mesenchymal lineages, e.g., chondro-osteoblastic (bone and cartilage), osteoblastic (bone), chondroblastic (cartilage), myocytic (muscle), tenocytic (tendon), fibroblastic (connective tissue), adipocytic (fat) and stromogenic (marrow stroma) lineage. MSC may be isolated from a biological sample, preferably a biological sample of a human subject, e.g., bone marrow, trabecular bone, blood, umbilical cord, placenta, foetal yolk sac, skin (dermis), specifically foetal and adolescent skin, periosteum, dental pulp, tendon and adipose tissue.

The term "MSC" also encompasses the progeny of MSC, e.g., progeny obtained by in vitro or ex vivo proliferation (propagation/expansion) of MSC obtained from a biological sample of an animal or human subject.

In particular embodiments, the growth medium is growth medium suitable for culturing pluripotent stem cells, preferably mesenchymal stem cells.

In particular embodiments, the tissue is a tissue selected from the group consisting of liver tissue, brain tissue and bone tissue.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The herein disclosed aspects and embodiments of the invention are further supported by the following non-limiting examples.

EXAMPLES

Example 1. Method for Preparing Human Platelet Releasates as Taught Herein

1. Materials and Methods

Platelet Concentrate

Expired platelet concentrates (PC) prepared and approved for transfusion were used in the preparation of human platelet releasate (hPR). In Flanders (Belgium), PCs are expired when the PC is not transfused within five days post donation.

Method of Preparation 4 different combinations of PC (comprising about 62.5% (v/v) platelet additive solution), $CaCl_2$ and/or soda-lime glass beads were prepared:

- 15 mM $CaCl_2$ was added to 40 ml of PC in a 50 ml plastic tube (combination 1);
- 4 mM $CaCl_2$ was added to 40 ml of PC in a 50 ml plastic tube (combination 2);
- 10 g of glass beads were added to 40 ml of PC in a 50 ml plastic tube (combination 3); or
- 10 g of glass beads and 4 mM $CaCl_2$ were added to 40 ml of PC in a 50 ml plastic tube (combination 4).

All 4 combinations were allowed to coagulate for a period of 3 hours at room temperature.

The soda-lime glass beads had a diameter of 3 mm.

2. Results

Figure 1:
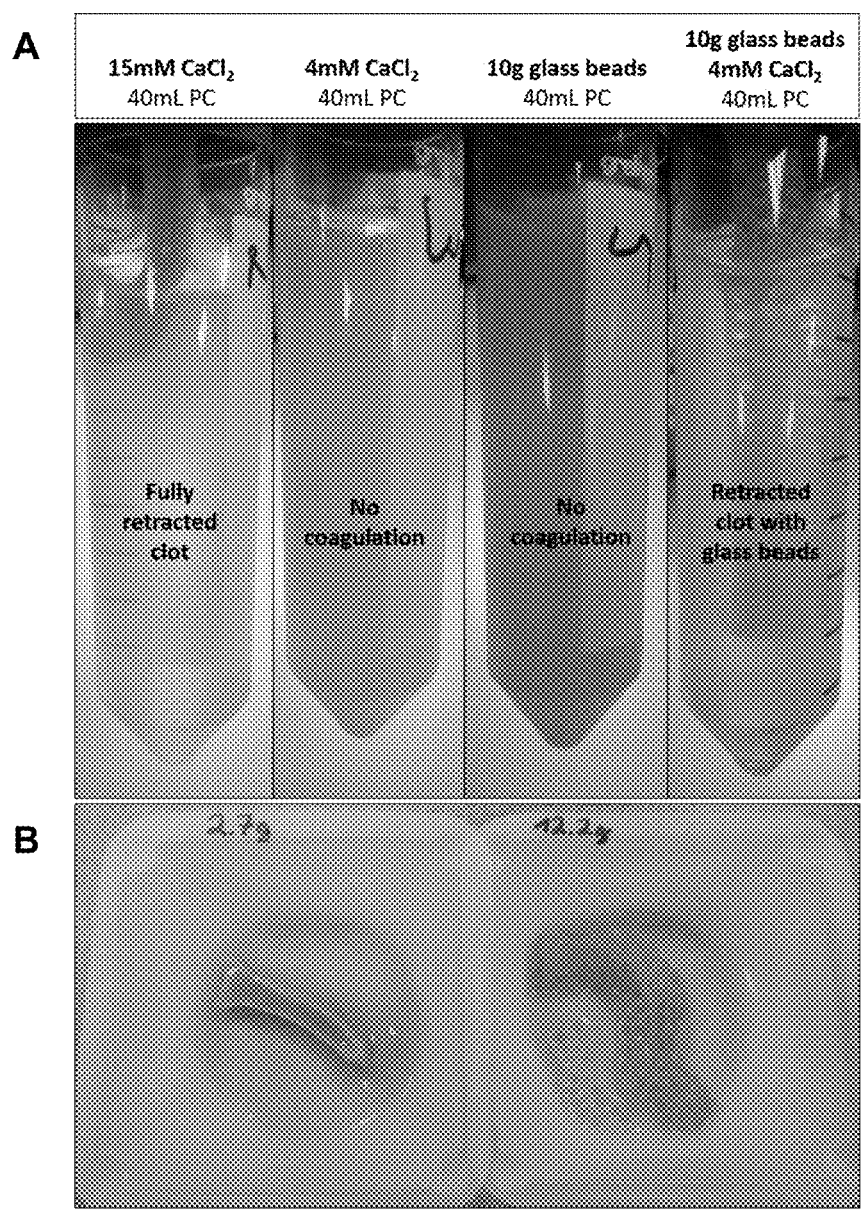
FIG. 1. (A) Coagulation of platelet concentrate (PC) containing 30% (v/v) plasma with $CaCl_2$), alone or in combination with glass beads. (B) Coagulum obtained by combining 15 mM $CaCl_2$ and 40 ml of PC (left panel) or by combining 10 g glass beads, 4 mM $CaCl_2$) and 40 ml PC (right panel).

Only combination 1 and 4 formed a retracted coagulum and a platelet releasate was obtained (FIG. 1A-B). In combination 2 and 3 no coagulation was observed and no platelet releasate was obtained (FIG. 1A).

This indicates that a combination of soda-lime glass beads and $CaCl_2$ allows for a lower concentration of $CaCl_2$ (i.e. 4 mM) to prepare platelet releasate.

Example 2. Method for Preparing Human Platelet Releasates and Platelet Lysates as Taught Herein in a Closed System Glass Beads and $CaCl_2$ in the Same Containing Space A PC bag comprising 350 ml PC (comprising about 62.5% (v/v) platelet additive solution) was welded to a bag system (FIG. 2A) of which the primary transfer bag contained 70 g of soda-lime glass beads (3 mm diameter) resulting in 0.2 g soda-lime glass beads per ml and 3.5 mL of a 404 mM $CaCl_2$ solution in water (distilled and sterilized by autoclaving). Subsequently, the empty PC bag was welded off. The PC, $CaCl_2$ and beads were mixed by gentle rotation/agitation. The bag system comprising the PC, glass beads and $CaCl_2$ was placed label down on a table at room temperature to allow coagulation to take place for three hours. During this process, platelets become activated by thrombin generation during coagulation and thus release growth factors by granule exocytosis. The coagulum eventually retracted at which point fluid was expelled from the coagulum interior releasing additional growth factors from the forming clot (data not shown), thereby obtaining the platelet releasate. If clot retraction is complete, a stable coagulum of typically 9 cm in length by 6 cm in width is left, entrapping both glass beads as well as platelet remnants. Next, the bag system can be stored at $-80°$ C. for at least 24 hours until further use. After thawing, a platelet lysate will be obtained.

Glass Beads and $CaCl_2$ in Separate Containing Space

Figure 2:
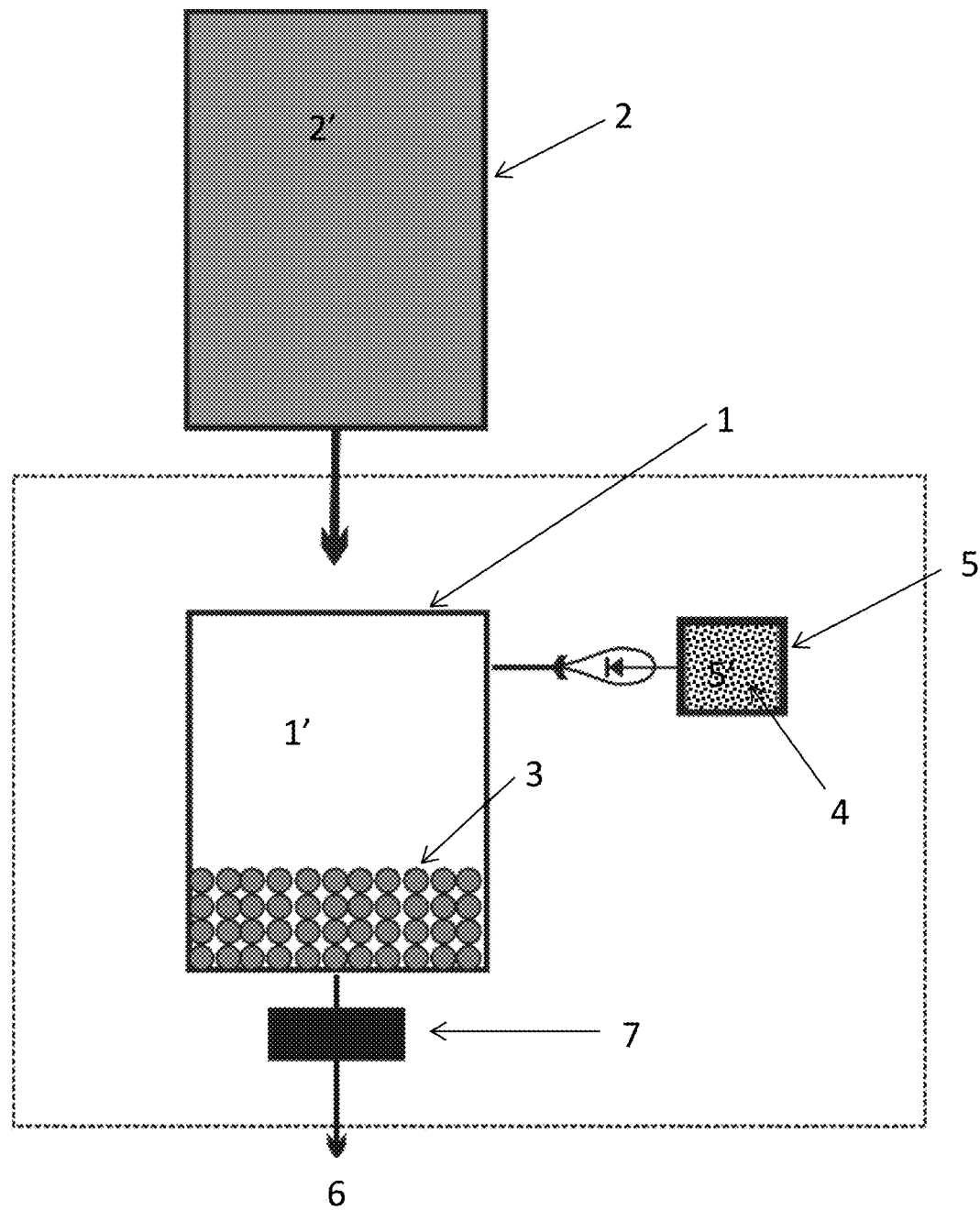
FIG. 2. System for preparing human platelet releasate (hPR) in a closed system. (A) PC is transferred from the containing space (2') of a PC bag (2) to the containing space (1') of a transfer bag (1) comprising glass beads (3) and $CaCl_2$ (4). Following transfer of the PC to the containing space (1'), the solution is allowed to coagulate. The transfer bag may be coupled to filtering means (7) to separate the platelet releasate obtained after coagulation from the glass beads, the coagulum and optionally from debris and particulate material. The transfer bag may be eluted in a recipient (6). (B) PC is transferred from the containing space (2') of a PC bag (2) to the containing space (1') of a transfer bag (1) comprising glass beads (3). The containing space (1') of the transfer bag (1) is linked to the containing space (5') of a pouch (5) comprising $CaCl_2$ (4) which is sealed by a break-away valve. Following transfer of the $CaCl_2$ to the containing space (1') of a transfer bag (1) comprising the PC and the glass beads, the solution is allowed to coagulate. The transfer bag may be coupled to filtering means (7) to separate the platelet releasate obtained after coagulation from the glass beads, the coagulum and optionally from debris and particulate material. The transfer bag may be eluted in a recipient (6).
Figure 3:
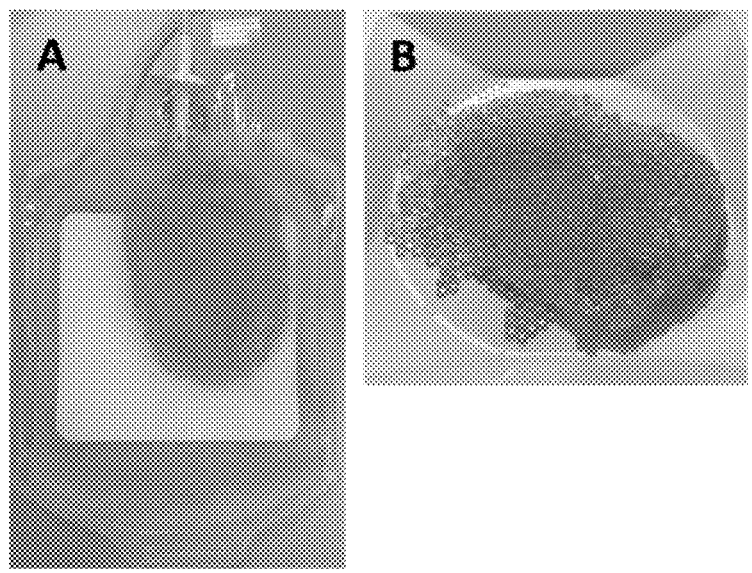
FIG. 3. Coagulum obtained by the methods as taught herein in a transfer bag (A) and removed from the bag (B).

A PC bag comprising 350 ml PC (comprising about 62.5% (v/v) platelet additive solution) was welded to a bag system (FIG. 2B) of which the primary transfer bag contained 70 g of soda-lime glass beads (3 mm diameter) resulting in 0.2 g soda-lime glass beads per ml. Next, the break-away cannula valve of a welded satellite bag that contains 3.5 mL of a 404 mM $CaCl_2$) solution in water (distilled and sterilized by autoclaving) was opened to release the content into the transfer bag containing the PC and the glass beads (FIG. 2B). Subsequently, the empty PC bag and the satellite bag were welded off. The PC, $CaCl_2$) and beads were mixed by gentle rotation/agitation. The bag system comprising the PC, glass beads and $CaCl_2$ was placed label down on a table at room temperature to allow coagulation to take place for three hours. During this process, platelets become activated by thrombin generation during coagulation and thus release growth factors by granule exocytosis. The coagulum eventually retracted at which point fluid was expelled from the coagulum interior releasing additional growth factors from the forming clot (FIG. 3A), thereby obtaining the platelet releasate. For illustration purposes, the coagulum was removed from the bag and shown in FIG. 3B. If clot retraction is complete, a stable coagulum of typically 9 cm in length by 6 cm in width is left, entrapping both glass beads as well as platelet remnants. Next, the bag system can be stored at $-80°$ C. for at least 24 hours until further use. After thawing, a platelet lysate will be obtained.

Example 3. Coagulation Parameters for Different Concentrations of Calcium Chloride and Glass Particles

1. Materials and Methods

Figure 5:
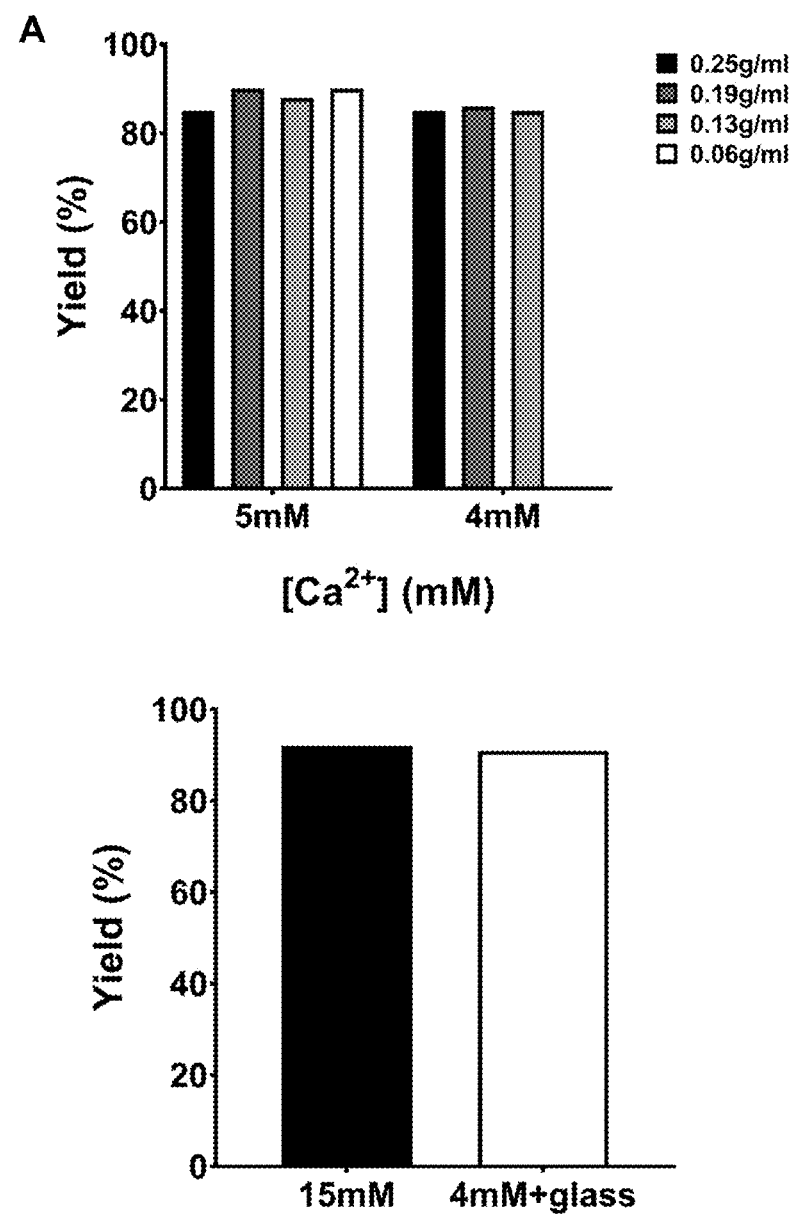
FIG. 5. (A) Releasate yield in PC (40 ml) coagulated with varying weights of glass beads and varying concentrations of Ca'. (B) Releasate yield in PC (350 ml) coagulated with 15 mM of $CaCl_2$ per ml PC, or with 4 mM of $CaCl_2$ and 0.20 g glass beads per ml PC.
Figure 8:
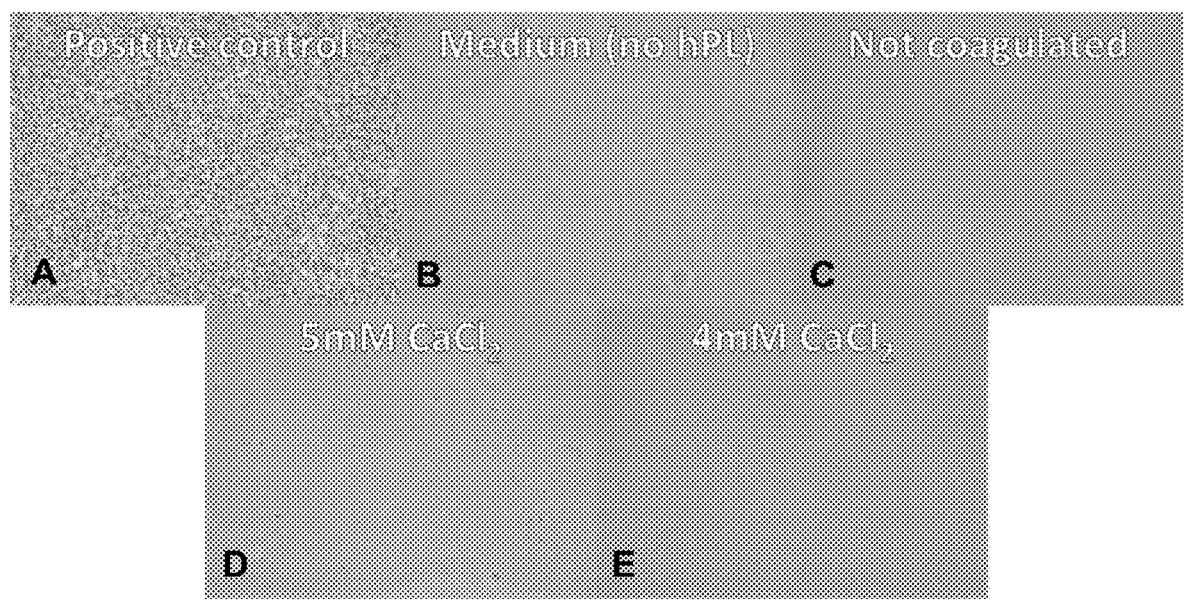
FIG. 8. Effect of adding human platelet releasate to DMEM cell culture medium. (A) growth medium with 10% (v/v) hPR prepared with 15 mM $CaCl_2$); (B) growth medium without hPR; (C) growth medium with 10% (v/v) hPR prepared without calcium; (D) growth medium with 10% (v/v) hPR prepared with 4 mM $CaCl_2$) and 0.20 g/mL glass beads; and (E) growth medium with 10% (v/v) hPR prepared with 5 mM $CaCl_2$) and 0.20 g/mL glass beads.

For the results shown in FIG. 5A, 8 different combinations of PC (comprising about 62.5% (v/v) platelet additive solution), $CaCl_2$) and/or soda-lime glass beads were prepared:

5 mM $CaCl_2$) and 2.5 g (combination 1), 5 g (combination 2), 7.5 g (combination 3) or 10 g (combination 4) of glass beads were added to 40 ml of PC;

4 mM $CaCl_2$ and 2.5 g (combination 5), 5 g (combination 6), 7.5 g (combination 7) or 10 g (combination 8) of glass beads were added to 40 ml of PC.

All 8 combinations were mixed by gentle inversion and allowed to coagulate for a period of 5 hours at room temperature.

For the results shown in FIG. 5B, hPR was prepared by: adding 15 mM $CaCl_2$ per ml PC (and no glass beads) to 350 ml of PC (comprising about 62.5% platelet additive solution); or adding 4 mM $CaCl_2$ per ml PC and 0.20 g glass beads per ml PC to 350 ml of PC (comprising about 62.5% platelet additive solution).

The soda-lime glass beads had a diameter of 3 mm.

The time to onset of retraction (FIG. 4) was determined by measuring the time (in minutes) between mixing and the moment that the coagulum effectively detached from the edges of the flask. The volume yield was determined by volumetry of the liquid fraction before and after coagulation. The volume after coagulation was divided by the initial volume and multiplied by 100 to calculate the releasate yield.

The concentration of $Ca^{2+}$ (i.e. calcium ions) in the platelet releasate was determined by blood gas analysis (RapidPoint 500, Siemens Healthcare, Erlangen, Germany) using built-in ion selective electrodes.

2. Results

Figure 4:
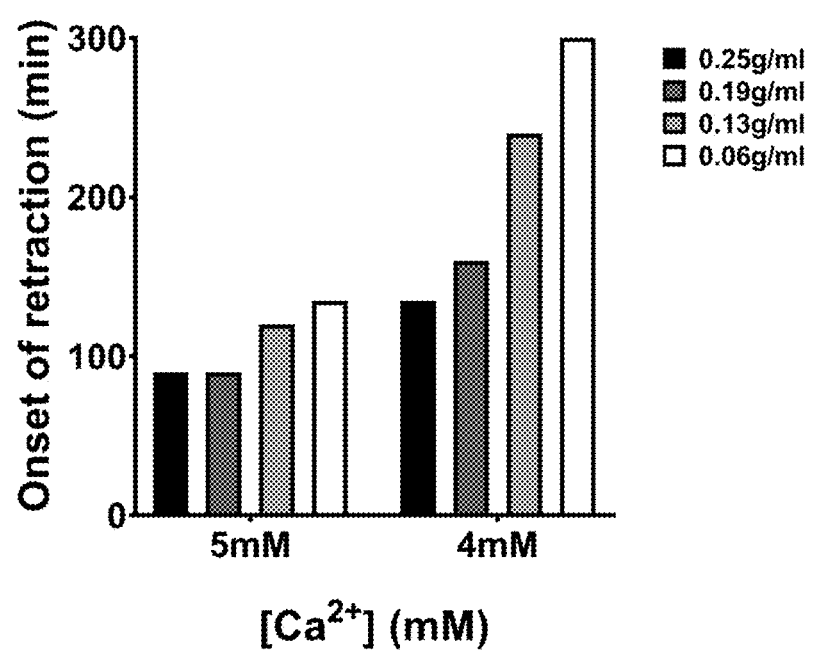
FIG. 4. Retraction speed at varying weights of glass beads and varying concentrations of Ca'.

The time to retraction of the coagulum shortens significantly by addition of increasing amounts of glass beads, in the context of two low concentrations of added $Ca^{2+}$ ions (i.e. 5 mM or 4 mM $CaCl_2$) (FIG. 4).

Releasate yield is not different among the tested combinations (FIG. 5A). Releasate yield is not different between a low concentration of $Ca^{2+}$ ions (i.e. 4 mM $CaCl_2$) combined with glass beads compared to a high concentration of $Ca^{2+}$ ions (i.e. 15 mM $CaCl_2$) without glass beads (FIG. 5B).

Figure 6:
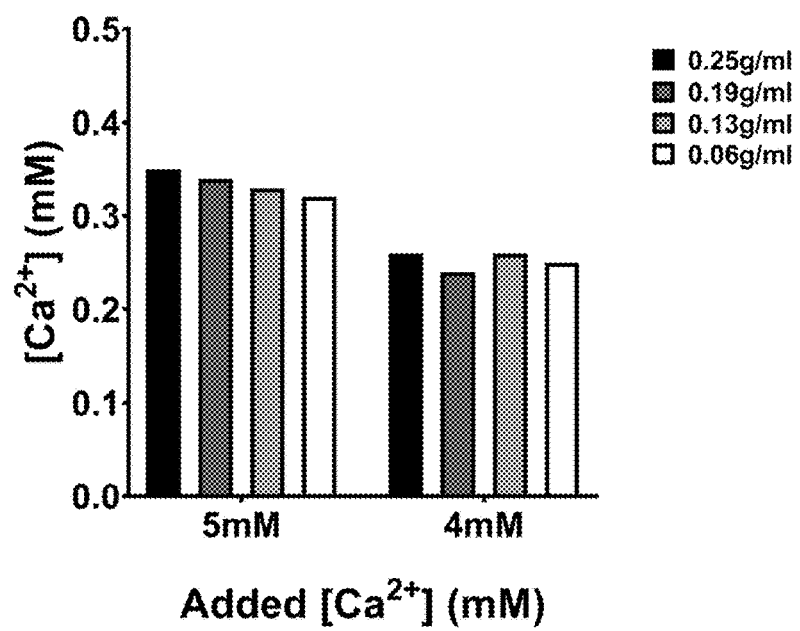
FIG. 6. The remaining concentration of $Ca^{2+}$ in the obtained platelet releasate after coagulation is completed. This is determined in a blood gas analyzer that uses a $Ca^{2+}$ ion selective electrode.

The residual $Ca^{2+}$ concentration after coagulation is lower in the platelet releasate obtained by all combinations with 4 mM $CaCl_2$ compared to all combinations with 5 mM $Ca^{2+}$ (FIG. 6). In addition, FIG. 6 shows that residual $Ca^{2+}$ concentration in the platelet releasate is not a function of the amount of glass beads used.

Example 4. Use of the Human Platelet Releasate as Taught Herein in Growth Media

Figure 7:
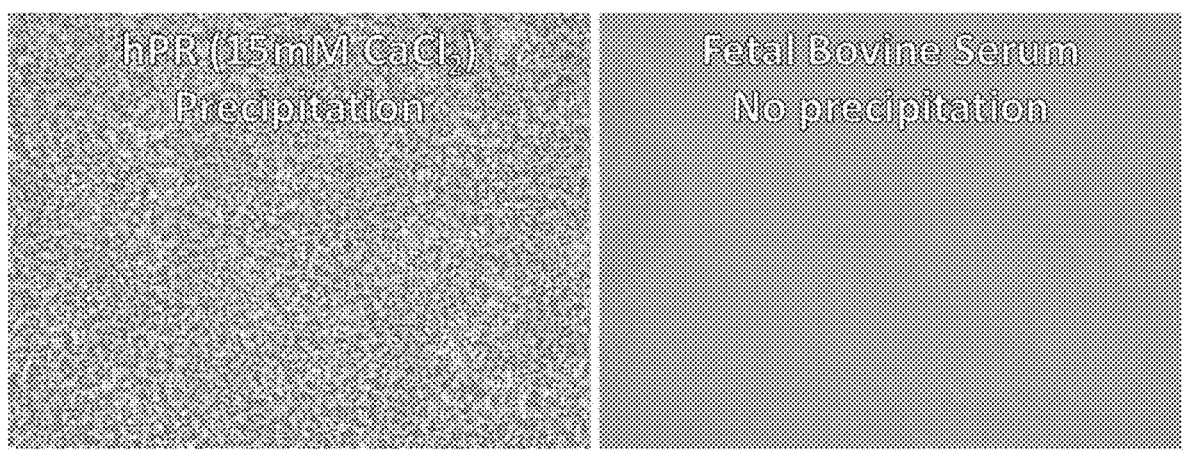
FIG. 7. Effect of adding 10% (v/v) human platelet releasate obtained from platelet concentrate comprising 65% platelet additive solution using 15 mM $CaCl_2$ without glass beads (left panel) or effect of adding fetal bovine serum (FBS) (right panel) to a Dulbecco's modified Eagle (DMEM) cell culture medium.

Most blood banks in the EU, Canada and Australia use an additive solution (like SSP+ from Macopharma, Tourcoing, FR) to replace the plasma fraction of PC by about 70% (v/v). This additive solution contains phosphate and carbonate anions. When human platelet releasate prepared by platelet activation methods using high concentrations of calcium (e.g. 15 mM of a calcium salt) is used in cell or tissue culture, the excess $Ca^{2+}$ ions will form chemical complexes with multivalent anions in the growth media to which hPR is added (FIG. 7, left panel). This leads to problems (e.g. reduced cell growth, stressed cells and even cell death) in subsequent cell or tissue culture. Control experiments using thrombin to cause coagulation did not cause precipitation and the addition of EDTA to the complexes made them dissolve. This indicates that the precipitations are calcium-dependent. Precipitations are not observed if fetal bovine serum (FBS) is added to growth medium (FIG. 7, right panel).

1. Materials and Methods

Preparation Growth Media

Dulbecco's modified Eagle medium (DMEM; Thermo Fisher Scientific) was supplemented with either
- 10% (v/v) hPR wherein the hPR was prepared with 15 mM $CaCl_2$ but without glass beads (growth medium 1, positive control);
- 0% (v/v) hPR (growth medium 5, medium (no hPR));
- 10% (v/v) human platelet lysate (hPL) wherein the hPL was prepared by standard freeze-thaw cycles (growth medium 2, not coagulated); or
- 10% (v/v) hPR wherein the hPR was prepared with 5 mM or 4 mM $CaCl_2$ and 0.2 g glass beads per mL of PC (growth media 3 and 4, 5 mM $CaCl_2$ and 4 mM $CaCl_2$).

2. Results

Growth medium 1 comprised precipitations (FIG. 8A), while growth media 5 did not comprise any precipitations (FIG. 8B).

Growth medium 2 did not comprise any precipitations (FIG. 8C). However, growth medium 2 will cause coagulation of the entire medium during cell culture. Due to the absence of added calcium, no coagulation step will occur while preparing the hPL. As a result hereof, when this hPL is added to the growth medium (which contains $Ca^{2+}$ ions) a spontaneous coagulation will take place during cell culture. The growth medium will stick as a gel to the bottom of the cell culture flask instead of remaining fluid. The reason therefore is that most growth media comprise calcium in concentrations sufficient to allow coagulation at 37° C. and 5% $CO_2$.

Growth media 3 and 4 do not comprise precipitations (FIG. 8D-E), indicating that the hPR prepared by the methods as taught herein overcomes the problem of the calcium-dependent precipitations typically observed when adding hPR prepared by standard methods to standard growth medium. In addition, the hPR prepared by the methods as taught herein overcomes the problem of coagulation after medium preparation typically observed when adding hPL or hPR prepared by standard methods to standard growth medium.

Example 5. Effect of the Human Platelet Releasate Prepared Using 15 mM and No Glass Beads on a Growth-Medium-Like Solution Ions playing a potential role in calcium precipitation were selected from the composition of a standard growth medium, namely DMEM, and a platelet additive solution, namely SSP+ in combination with exogenously added $CaCl_2$ (Table 1).

TABLE 1

|  | $HCO_3^-$ (mM) | $PO_4^{3-}$ (mM) | $Ca^{2+}$ (mM) |
|---|---|---|---|
| DMEM | 44.05 | 0.91 | 1.80 |
| SSP+ | / | 28.2 | / |
| $CaCl_2$ | / | / | 1500 |

In hPR prepared with 15 mM $CaCl_2$ without glass beads, a residual $Ca^{2+}$ concentration of 1.5 mM was measured after coagulation. Assuming the platelet-rich comprising composition from which the hPR was prepared comprised 70% (v/v) SSP+, the theoretical concentrations of the selected ions in hPR would be the following:
- 4 mM $HCO_3^-$
- 19.7 mM $PO_4^{3-}$
- 1.5 mM $Ca^{2+}$ Assuming a growth medium composed of 90% (v/v) DMEM and 10% (v/v) hPR, the theoretical concentrations of the selected ions in growth medium+hPR would be the following:
- 90% (v/v) DMEM+10% (v/v) hPR:
  - 39.6+0.4=40.0 mM $HCO_3^-$
  - 0.8+2.82=3.6 mM $PO_4^{3-}$
  - 1.62+0.15=1.77 mM $Ca^{2+}$ Experiments were conducted to detect precipitation in minimal ion compositions in conditions of cell culture (5% $CO_2$ and 37° C.). Ion compositions were prepared in water as indicated below and incubated in a cell incubator. Precipitation was detected by visual control using bright field microscopy:
1. $Ca^{2+}$ and $HCO_3^-$?
   - 44 mM $NaHCO_3$
   - 2 mM $CaCl_2$)
   No precipitation was observed.
2. $Ca^{2+}$ and $H_2PO_4^-$?
   - 3.73 mM $NaH_2PO_4$
   - 2 mM $CaCl_2$
   No precipitation was observed.
3. $Ca^{2+}$ and $HCO_3^-$ and $H_2PO_4^-$?
   - 44 mM $NaHCO_3$
   - 3.73 mM $NaH_2PO_4$
   - 2 mM $CaCl_2$
   Precipitation was observed.

The data show that precipitation of insoluble calcium salts at least requires the presence of both phosphate anions as well as bicarbonate anions, in the physical and chemical conditions tested above. The data also suggest that these anions are sufficient to cause precipitation, indicating that any commercial culture medium containing these anions (at least in the concentrations tested) would suffer from insoluble calcium salt precipitations using 10% (v/v) hPR prepared with >15 mM $CaCl_2$ and no glass beads.

Example 6. Effect of the Human Platelet Releasate as Taught Herein on Cell Growth 1. Materials and Methods Adipose tissue-derived mesenchymal stem cells (MSC) were cultured in DMEM growth medium supplemented with different types of hPR or hPL at 10% (v/v) or FBS 10% (v/v). The different types of hPR include:
- hPL prepared by two freeze-thaw cycles with subsequent centrifugation ('standard');
- hPR prepared with 5 mM $CaCl_2$) and 0.2 g glass beads per mL of PC ('$CaCl_2$+glass');
- hPL (nLiven PR™) of Cook Regentec ('Competitor 1');
- hPL (PLTMax™; SCM141) of EMD Merck Millipore ('Competitor 2'); and
- hPR (Multipl' range; reference number BC0190020/BC0190030) of Macopharma (Competitor 3').

The cell doubling time of the MSC was determined by cell counting in a hemacytometer (type Malassez) as a function of culture time.

2. Results

Figure 9:
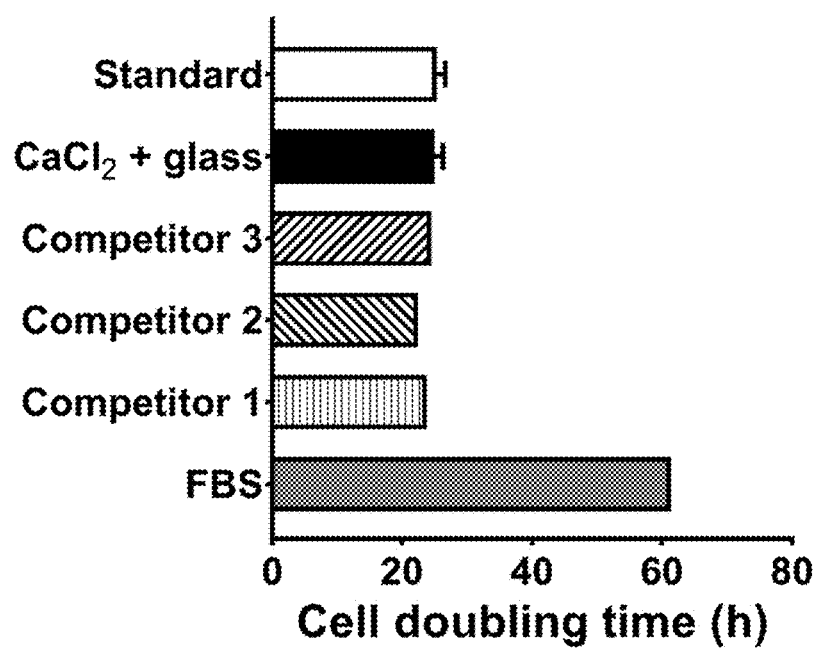
FIG. 9. Cell doubling time of adipose tissue-derived mesenchymal stem cells (MSC) cultured in DMEM growth medium supplemented with different types of hPR at 10%

FIG. 9 shows that the cell doubling time for '$CaCl_2$+glass' is about 2.4-fold faster compared to FBS. Furthermore, the cell doubling time for '$CaCl_2$+glass' is more or less the same as the cell doubling time for 'Standard' hPR and the hPR of three commercial competitors.

Example 7. Effect of the Human Platelet Releasate as Taught Herein on Cell Stress 1. Materials and Methods Adipose tissue-derived mesenchymal stem cells (MSC) were cultured in DMEM growth medium supplemented with 10% (v/v) hPR prepared with 15 mM $CaCl_2$ without glass beads or 10% (v/v) hPR prepared with 4 mM $CaCl_2$ and 0.20 g glass beads per ml PC.

The effect on cell stress and cell death was determined microscopically.

2. Results

FIG. 10 shows that MSCs cultured in DMEM growth medium supplemented with 10% (v/v) hPR prepared with 15 mM $CaCl_2$ without glass beads (FIG. 10A) suffer from cell stress and even cell death, while MSCs cultured in DMEM growth medium supplemented with 10% (v/v) hPR prepared with 4 mM $CaCl_2$ and 0.20 g glass beads per ml PC appear healthy (FIG. 10B).

Example 8. Effect of Different Types of Silica-Based Particles on Coagulation Time Paired PC (350 mL, comprising about 62.5% (v/v) platelet additive solution) were added to bags containing 0.20 g/ml, 0.15 g/ml or 0.10 g/ml of borosilicate glass beads. 6 mM, 5 mM or 4 mM of $CaCl_2$) was added to the mixture of PC and glass beads. The time to complete retraction was recorded. The PC was considered "not retracted" when >3 h of recording was required (FIG. 11, indicated by an 'X'). Successful retraction is indicated in FIG. 11 by a 'V'.

The data show that in the presence of borosilicate glass, more than 4 mM of $CaCl_2$ is required to obtain a complete retraction in less than 3 h while in such conditions using soda-lime glass, all of the 20 PC were successfully retracted in less than 3 h. In the conditions with 5 mM $CaCl_2$) successful retraction of PC was found, but taking longer (3 h on average) than in the presence of equal amounts of soda-lime glass (2 h30 on average).

Example 9. Method for Preparing Human Platelet Releasates as Taught Herein from Platelet Concentrate which does not Comprise Platelet Additive Solution Platelet concentrates were prepared in 100% (v/v) plasma, without addition of a platelet additive solution. 0.25 g/ml, 0.15 g/ml or 0.05 g/ml of soda-lime glass beads and 10 mM, 8 mM, 6 mM, 4 mM or 2 mM of $CaCl_2$ were added to 40 ml of PC in 50 mL falcon tubes. Clot retraction time was monitored during 21 h. The PC was considered "not retracted" when >21 h of recording was required (FIG. 12, indicated by a 'X'). Successful retraction <3 h is indicated by a 'V' in FIG. 12. Clot retraction between 3 h and 21 h is indicated by an open circle in FIG. 12.

The data show that in the presence of 100% (v/v) plasma clot retraction is not significantly faster compared to historic samples of PC prepared in about 35% (v/v) plasma and about 65% (v/v) additive solution.

Example 10. Comparative Analysis of Final Ionized Calcium Concentrations in Platelet Releasates Produced According to the Invention and Prior Art Platelet Releasates The concentration of $Ca^{2+}$ (ionized calcium) in platelet releasates prepared according to cited prior art. In a paired experiment platelet concentrates in additive solution (PAS-plasma) or in pure plasma (Plasma) were treated with the claimed method (TReC) or those from prior art documents: Ming-Li Chou et al., 2014, PLOS ONE vol. 9(6), 19 Jun. 2014, page e99145 (D1), WO2013/003356 (D2), and Martina Bernardi et al., 2017, J. of Translatioal Medicine, vol. 15(1) (D3). The respective starting Ca' concentrations (i.e. the amount of calcium added) are indicated in the legend. In the resulting end product, the $Ca^{2+}$ concentration was measured and is given in FIG. 13. As shown by the black bars, the concentration of $Ca^{2+}$ is significantly lower for the claimed method compared to competing methods D1-D3. The dotted line represents the maximal $Ca^{2+}$ concentration allowed in pure platelet releasate to prevent precipitate phosphate-calcium complexes in typical tissue culture media compositions.

Compared to the high-calcium method of Ming-Li Chou et al., 2014, the method of the invention results in platelet releasates that are not prone to calcium-phosphate precipitation when used in cell culturing medium as can be shown in the comparison depicted in FIG. 14. Precipitation of chemical phosphate ($HPO_4^{2-}$, $H_2PO_4^-$ & $PO_4^{3-}$) complexes with calcium ($Ca^{2+}$) in tissue culture media. Tissue culture medium (DMEM with pre-added $Ca^{2+}$) was supplemented with 10% platelet releasate prepared from platelet concentrates containing additive solution as the source of phosphate anions. Two different methods for platelet releasate preparation were used: our low $Ca^{2+}$ method (A) or the D1 prior art high $Ca^{2+}$ method (B). After 24 hours incubation at 37° C. and $CO_2$ (pCO$_2$ 5%), phosphate-calcium complexes were visible using bright field microscopy (200×) only in condition B. The residual concentrations of $Ca^{2+}$ (closed bars) and $PO_4^{3-}$ (open bars) ions in the medium is indicated in the graph (lower panel). The dotted line represents the theoretical solubility of $Ca^{2+}$ with $PO_4^{3-}$ at pH 7.4 and ideal thermodynamic conditions.

This data clearly shows the beneficial effect of using the method according to the invention for preparing platelet releasates with reduced risk of obtaining precipitation in cell culture medium avoiding cellular damage and avoiding influence of calcium ions on e.g. signaling pathways.

The invention claimed is:

1. A method for preparing platelet releasate from a sample of a platelet-rich blood composition obtained from a subject, said method comprising the steps of
    a) contacting said sample with from 0.010 g to 0.60 g of glass particles per ml of said sample and from 1.0 µmol to 12.0 µmol of one or more water-soluble calcium salts per ml of said sample thereby obtaining a mixture; and
    b) allowing the mixture obtained in step a) to coagulate, thereby obtaining a coagulum and platelet releasate, wherein the subject is a mammal.

2. A system for preparing a platelet releasate, comprising a first container (1) having a first containing space (1'), wherein said first containing space (1'):
    is configured to receive a quantity ($Q_{bc}$) of a platelet-rich blood composition comprised in a second containing space (2') of a second container (2);
    holds a quantity ($Q_{gp}$) of glass particles (3); and
    holds a quantity ($Q_{cc}$) of one or more water-soluble calcium salts (4) or is configured to receive a quantity ($Q_{cc}$) of one or more water-soluble calcium salts (4) held by a third containing space (5') of a third container (5),
    wherein the ratio $Q_{gp}:Q_{bc}$ is from 0.010 to 0.60 g per ml of said platelet-rich blood composition, and the ratio $Q_{cc}:Q_{bc}$ is from 1.0 to 12.0 µmol per ml of said platelet-rich blood composition, and
    wherein the platelet-rich blood composition has been obtained from a mammal.

3. The system according to claim 2, wherein the ratio $Q_{gp}:Q_{bc}$ is from 0.10 to 0.40 and the ratio $Q_{cc}:Q_{bc}$ is from 3.0 to 8.0.

4. The method for preparing platelet releasate or platelet lysate according to claim 1, comprising contacting said sample with a system comprising a first container (1) having a first containing space (1') wherein said first containing space (1'):
    is configured to receive a quantity ($Q_{bc}$) of the sample comprised in a second containing space (2') of a second container (2);
    holds a quantity ($Q_{gp}$) of glass particles (3); and
    holds a quantity ($Q_{cc}$) of one or more water-soluble calcium salts (4) or is configured to receive a quantity ($Q_{cc}$) of one or more water-soluble calcium salts (4) held by a third containing space (5') of a third container (5);
    wherein the ratio $Q_{gp}:Q_{bc}$ is from 0.010 to 0.60 g per ml of said platelet-rich blood composition, and the ratio $Q_{cc}:Q_{bc}$ is from 1.0 to 12.0 µmol per ml of said platelet-rich blood composition.

5. The method for preparing platelet releasate according to claim 1, additionally comprising the step of:
    c) recovering the platelet releasate obtained in step b) from the mixture.

6. The method according to claim 1, wherein said sample is contacted with from 0.10 g to 0.40 g of glass particles per ml of said sample and from 3.0 µmol to 8.0 µmol of one or more water-soluble calcium salts per ml of said sample.

7. The method according to claim 1, wherein said glass particles have an average diameter from 1.0 mm to 5.0 mm.

8. The method according to claim 1, wherein said glass particles are silica-based glass particles.

9. The method according to claim 1, wherein said one or more water-soluble calcium salts are selected from the group consisting of calcium chloride, calcium hydroxide, calcium acetate, calcium carbonate, calcium bicarbonate, calcium chlorate, calcium perchlorate, calcium sulfate, calcium nitrate, calcium nitrite, calcium lactate, calcium glubionate, calcium gluceptate and calcium gluconate or mixtures thereof.

10. The method according to claim 1, wherein said platelet-rich blood composition is selected from platelet concentrate, plasma and whole blood.

11. The method according to claim 5, further comprising a step of lysing the platelets present in the obtained coagulum and/or platelet releasate obtained in step b), thereby obtaining a platelet lysate.

12. The system according to claim 2, wherein said glass particles have an average diameter from 1.0 mm to 5.0 mm.

13. The system according to claim 2, wherein said glass particles are silica-based glass particles.

14. The method according to claim 1, wherein said glass particles are soda-lime-silica or soda-lime glass particles, sodium borosilicate glass particles, aluminosilicate glass particles, lead-oxide glass particles or fused-silica glass particles.

15. The system according to claim 2, wherein said glass particles are soda-lime-silica or soda-lime glass particles, sodium borosilicate glass particles, aluminosilicate glass particles, lead-oxide glass particles or fused-silica glass particles.

16. The method of claim 1, comprising in b), allowing the obtained mixture to coagulate such that the obtained platelet releasate comprises a residual $Ca^{2+}$ concentration of 1 mM or less.

17. The system of claim 2, wherein the platelet releasate comprises a residual $Ca^{2+}$ concentration of 1 mM or less.

* * * * *